US010138271B2

(12) United States Patent
Schlom et al.

(10) Patent No.: US 10,138,271 B2
(45) Date of Patent: Nov. 27, 2018

(54) NATIVE AND AGONIST CTL EPITOPES OF THE MUC1 TUMOR ANTIGEN

(71) Applicant: The United States of America, as represented by the Secretary, Department of Health and Human Services, Washington, DC (US)

(72) Inventors: Jeffrey Schlom, Potomac, MD (US); Kwong-Yok Tsang, Bethesda, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/370,595

(22) PCT Filed: Jan. 3, 2013

(86) PCT No.: PCT/US2013/020058
§ 371 (c)(1),
(2) Date: Jul. 3, 2014

(87) PCT Pub. No.: WO2013/103658
PCT Pub. Date: Jul. 11, 2013

(65) Prior Publication Data
US 2014/0363495 A1 Dec. 11, 2014

Related U.S. Application Data

(60) Provisional application No. 61/582,723, filed on Jan. 3, 2012.

(51) Int. Cl.
| A61K 35/12 | (2015.01) |
| A61K 48/00 | (2006.01) |
| C07K 7/06 | (2006.01) |
| A61K 39/00 | (2006.01) |
| C07K 14/47 | (2006.01) |
| A61K 9/127 | (2006.01) |
| A61K 35/17 | (2015.01) |
| A61K 38/19 | (2006.01) |
| A61K 45/06 | (2006.01) |
| A61K 38/00 | (2006.01) |

(52) U.S. Cl.
CPC ............ *C07K 7/06* (2013.01); *A61K 9/127* (2013.01); *A61K 35/17* (2013.01); *A61K 38/193* (2013.01); *A61K 39/0011* (2013.01); *A61K 45/06* (2013.01); *C07K 14/4727* (2013.01); *C07K 14/4748* (2013.01); *A61K 38/00* (2013.01); *A61K 2039/5154* (2013.01); *A61K 2039/5158* (2013.01); *A61K 2039/585* (2013.01); *Y02A 50/466* (2018.01)

(58) Field of Classification Search
None
See application file for complete search history.

(56) References Cited

U.S. PATENT DOCUMENTS

| 5,827,666 A | 10/1998 | Finn et al. |
| 6,548,643 B1 | 4/2003 | McKenzie et al. |
| 6,600,012 B1 | 7/2003 | Agrawal et al. |
| 7,084,249 B1 | 8/2006 | Eisenbach et al. |
| 7,696,306 B2 | 4/2010 | Hollingsworth et al. |
| 7,999,071 B2 | 8/2011 | Schlom et al. |
| 8,901,093 B2 | 12/2014 | Panicali et al. |
| 8,933,041 B2 | 1/2015 | Panicali et al. |
| 2011/0319869 A1 | 12/2011 | Schlom et al. |

FOREIGN PATENT DOCUMENTS

| WO | WO 2005058937 A2 * | 6/2005 |
| WO | WO 2010037395 A2 | 4/2010 |
| WO | WO 2013025972 A1 | 2/2013 |

OTHER PUBLICATIONS

Verma et al. (1997, Nature, vol. 389, pp. 239-242).*
Anderson et al. (1998, Nature, vol. 392, pp. 25-30).*
Palu et al. (1999, Journal of Biotechnology, vol. 68, pp. 1-13).*
Xu et al (Journal of Pharmaceutical Sciences, 2011. vol. 100, No. 1, pp. 38-52).*
Beatty et al., *Cancer Prev. Res.*, 3(4): 438-446 (2010).
European Patent Office, International Search Report in PCT Application US2013020058 (dated Jun. 26, 2013).
International Bureau of WIPO, International Preliminary Report on Patentability in PCT Application US2013020058 (dated Jul. 17, 2014).
Chen et al., "A simple but effective cancer vaccine consisting of an antigen and a cationic lipid", *Cancer Immunol. Immunother* 57:4, 517-530 (2008).
Chen et al., "Induction of Cytotoxic T-Lymphocytes and Antitumor Activity by a Liposomal Lipopeptide Vaccine", *Molecular Pharmaceutics*, 5:3, 464-471 (2008).
Kantoff et al., "Overall Survival Analysis of a Phase II Randomized Controlled Trial of a Poxviral-Based PSA-Targeted Immunotherapy in Metastatic Castration-Resistant Prostate Cancer", *Journal of Clinical Oncology*, 28:7, 1099-1105 (2010).
Kim et al., "Poxviral vectors for cancer immunotherapy", *Expert Opin Biol Ther.*, 12:4, 463-478 (2012).
Kimura et al., "MUC1 immunotherapy is here to stay.", *Expert Opin Biol Ther.*, 13:1, 35-49 (2013).
Korsholm et al., "The adjuvant mechanism of cationic dimethyldioctadecylammonium liposomes", *Immunology*, 121, 216-226 (2007).

(Continued)

*Primary Examiner* — Celine X Qian
(74) *Attorney, Agent, or Firm* — Leydig, Voit & Mayer, Ltd.

(57) ABSTRACT

The invention provides peptides comprising a human cytolytic T lymphocyte (CTL) epitope from the human tumor-associated antigen (TAA) mucin 1 (MUC1) and analogs thereof, which can be used in vaccine prevention or therapy of cancer, as well as a nucleic acid encoding the peptide, a vector comprising the nucleic acid, a cell comprising the peptide, nucleic acid, or vector, and compositions thereof.

25 Claims, 5 Drawing Sheets

Figure 1A:
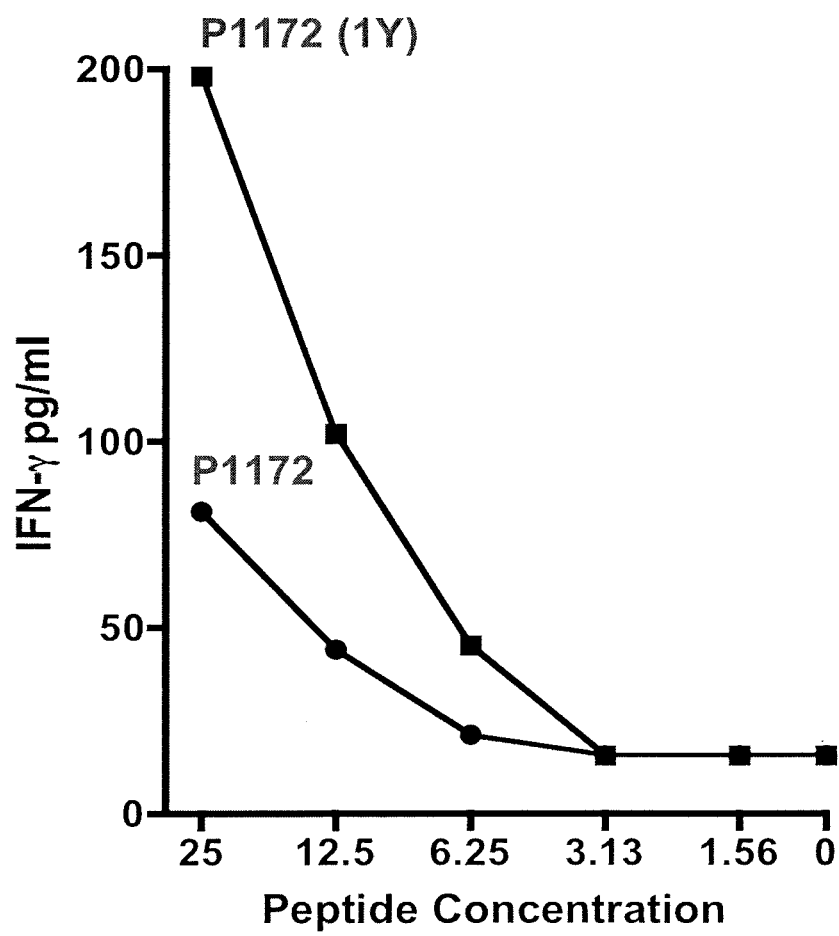

Specification includes a Sequence Listing.

(56) References Cited

OTHER PUBLICATIONS

Melero et al., "Therapeutic vaccines for cancer: an overview of clinical trials", *Nature Reviews Clinical Oncology*, 11, 509-524 (2014).

Morse et al., "A Randomized Phase II Study of Immunization with Dendritic Cells Modified with Poxvectors Encoding CEA and MUC1 Compared with the Same Poxvectors Plus GM-CSF for Resected Metastatic Colorectal Cancer", *Ann Surg.*, 258:4, 879-886 (2013).

Vasievich et al., "Trp2 Peptide Vaccine Adjuvanted with ®-DOTAP Inhibits Tumor Growth in an Advanced Melanoma Model", *Molecular Pharmaceutics* 9:2, 261-268 (2012).

\* cited by examiner

SEQUENCE LISTING

```
<160> NUMBER OF SEQ ID NOS: 32

<210> SEQ ID NO 1
<211> LENGTH: 10
<212> TYPE: PRT
<213> ORGANISM: Artificial Sequence
<220> FEATURE:
<223> OTHER INFORMATION: Synthetic

<400> SEQUENCE: 1

Ala Leu Ala Ile Val Tyr Leu Ile Ala Leu
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic

<400> SEQUENCE: 2

Tyr Leu Ala Ile Val Tyr Leu Ile Ala Leu
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: wherein Xaa is Ala or Tyr

<400> SEQUENCE: 3

Xaa Leu Ala Ile Val Tyr Leu Ile Ala Leu
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic

<400> SEQUENCE: 4

Tyr Leu Ile Ala Leu Ala Val Cys Gln Cys
1               5                   10

<210> SEQ ID NO 5
<211> LENGTH: 10
<212> TYPE: PRT
<213> ORGANISM: Artificial Sequence
```

```
<220> FEATURE:
<223> OTHER INFORMATION: Synthetic

<400> SEQUENCE: 5

Tyr Leu Ile Ala Leu Ala Val Cys Gln Val
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: wherein Xaa is Cys or Val

<400> SEQUENCE: 6

Tyr Leu Ile Ala Leu Ala Val Cys Gln Xaa
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Synthetic

<400> SEQUENCE: 7

Ser Leu Ser Tyr Thr Asn Pro Ala Val
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

Tyr Leu Ser Tyr Thr Asn Pro Ala Val
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: wherein Xaa is Ser or Tyr

<400> SEQUENCE: 9

Xaa Leu Ser Tyr Thr Asn Pro Ala Val
1               5

<210> SEQ ID NO 10
<211> LENGTH: 10
<212> TYPE: PRT
<213> ORGANISM: Artificial Sequence
<220> FEATURE:
<223> OTHER INFORMATION: Synthetic
```

```
<400> SEQUENCE: 10

Ala Leu Phe Ile Val Tyr Leu Ile Ala Lys
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: wherein Xaa is Ala or Phe
<220> FEATURE:
<221> NAME/KEY: MISC_FEATURE
<222> LOCATION: (10)..(10)
<223> OTHER INFORMATION: wherein Xaa is Leu or Lys

<400> SEQUENCE: 11

Ala Leu Xaa Ile Val Tyr Leu Ile Ala Xaa
1               5                   10

<210> SEQ ID NO 12
<211> LENGTH: 9
<212> TYPE: PRT
<213> ORGANISM: Artificial Sequence
<220> FEATURE:
<223> OTHER INFORMATION: Synthetic

<400> SEQUENCE: 12

Ser Thr Asp Arg Ser Pro Tyr Glu Lys
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic

<400> SEQUENCE: 13

Ser Leu Tyr Arg Ser Pro Tyr Glu Lys
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic

<400> SEQUENCE: 14

Ser Leu Phe Arg Ser Pro Tyr Glu Lys
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: wherein Xaa is Thr or Leu
```

```
<220> FEATURE:
<221> NAME/KEY: MISC_FEATURE
<222> LOCATION: (3)..(3)
<223> OTHER INFORMATION: wherein Xaa is Asp, Tyr, or Phe

<400> SEQUENCE: 15

Ser Xaa Xaa Arg Ser Pro Tyr Glu Lys
1               5

<210> SEQ ID NO 16
<211> LENGTH: 10
<212> TYPE: PRT
<213> ORGANISM: Artificial Sequence
<220> FEATURE:
<223> OTHER INFORMATION: Synthetic

<400> SEQUENCE: 16

Gly Leu Phe Asp Glu Tyr Leu Glu Met Val
1               5                   10

<210> SEQ ID NO 17
<211> LENGTH: 9
<212> TYPE: PRT
<213> ORGANISM: Artificial Sequence
<220> FEATURE:
<223> OTHER INFORMATION: Synthetic

<400> SEQUENCE: 17

His Leu Phe Gly Tyr Ser Trp Tyr Lys
1               5

<210> SEQ ID NO 18
<211> LENGTH: 10
<212> TYPE: PRT
<213> ORGANISM: Artificial Sequence
<220> FEATURE:
<223> OTHER INFORMATION: Synthetic

<400> SEQUENCE: 18

Leu Leu Val Leu Val Cys Val Leu Val Ala
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic

<400> SEQUENCE: 19

Leu Leu Val Leu Val Ile Val Leu Val Lys
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthetic

<400> SEQUENCE: 20

Leu Leu Val Leu Val Cys Val Leu Val Lys
1               5                   10
```

```
<210> SEQ ID NO 21
<211> LENGTH: 9
<212> TYPE: PRT
<213> ORGANISM: Artificial Sequence
<220> FEATURE:
<223> OTHER INFORMATION: Synthetic

<400> SEQUENCE: 21

Gly Gln Leu Asp Ile Phe Pro Ala Arg
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic

<400> SEQUENCE: 22

Gly Leu Leu Asp Ile Phe Pro Ala Lys
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic

<400> SEQUENCE: 23

Gly Gln Leu Asp Ile Phe Pro Ala Arg
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic

<400> SEQUENCE: 24

Gly Leu Leu Asp Ile Phe Pro Ala Lys
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic

<400> SEQUENCE: 25

Ser Leu Tyr Asn Thr Val Ala Thr Leu
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: wherein Xaa is Ser or Tyr
<220> FEATURE:
<221> NAME/KEY: MISC_FEATURE
<222> LOCATION: (2)..(2)
<223> OTHER INFORMATION: wherein Xaa is Thr or Leu
```

```
<220> FEATURE:
<221> NAME/KEY: MISC_FEATURE
<222> LOCATION: (8)..(8)
<223> OTHER INFORMATION: wherein Xaa is Asn or Gly

<400> SEQUENCE: 26

Xaa Xaa Ala Pro Pro Ala His Xaa Val
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic

<400> SEQUENCE: 27

Ser Thr Ala Pro Pro Ala His Asn Val
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic

<400> SEQUENCE: 28

Ser Thr Ala Pro Pro Ala His Gly Val
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic

<400> SEQUENCE: 29

Tyr Leu Ala Pro Pro Ala His Gly Val
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: wherein Xaa is Ala or Tyr
<220> FEATURE:
<221> NAME/KEY: MISC_FEATURE
<222> LOCATION: (2)..(2)
<223> OTHER INFORMATION: wherein Xaa is Pro or Leu
<220> FEATURE:
<221> NAME/KEY: MISC_FEATURE
<222> LOCATION: (9)..(9)
<223> OTHER INFORMATION: wherein Xaa is Gly or Val

<400> SEQUENCE: 30

Xaa Xaa Asp Thr Arg Pro Ala Pro Xaa
1               5

<210> SEQ ID NO 31
<211> LENGTH: 9
<212> TYPE: PRT
<213> ORGANISM: Artificial Sequence
```

```
<220> FEATURE:
<223> OTHER INFORMATION: Synthetic

<400> SEQUENCE: 31

Ala Pro Asp Thr Arg Pro Ala Pro Gly
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Tyr Leu Asp Thr Arg Pro Ala Pro Val
1               5
```

US 10,138,271 B2

NATIVE AND AGONIST CTL EPITOPES OF THE MUC1 TUMOR ANTIGEN

CROSS-REFERENCE TO RELATED APPLICATIONS

This patent application is a U.S. National Phase of International Patent Application No. PCT/US2013/020058, filed Jan. 3, 2013, which claims the benefit of U.S. Provisional Patent Application No. 61/582,723, filed Jan. 3, 2012, which are incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 7,414 Byte ASCII (Text) file named "718026_ST25.txt," created on Jun. 16, 2014.

BACKGROUND OF THE INVENTION

MUC1 (CD227) is a type I membrane glycoprotein composed of heterodimers of a large N-terminal subunit (MUC1-N) covalently bound to a small C-terminal subunit (MUC1-C). MUC1-N is completely extracellular, heavily glycosylated, and composed almost entirely of the 20-amino-acid variable number of tandem repeats (VNTR) domain. MUC1-C consists of a short extracellular domain, a transmembrane domain, and a cytoplasmic tail or domain (MUC1-CD).

MUC1 is normally expressed on the apical surface of epithelial cells and in a small subset of nonepithelial cells such as hematopoietic cells and activated T cells. Its major function in healthy epithelia is to provide lubrication and a physical barrier against chemical and microbial agents. Its physiologic role in other cell types is unclear.

It has been demonstrated that many human carcinomas (such as ovarian, breast, pancreatic, colorectal, and prostate) and hematologic malignancies (multiple myeloma and some B-cell non-Hodgkin's lymphomas) aberrantly overexpress MUC1. In contrast to its clustered expression in normal tissues, MUC1 is uniformly distributed over the entire surface of tumor cells. Moreover, MUC1 is generally underglycosylated in tumors, exposing novel and potentially antigenic epitopes of the protein core to the immune system. MUC1 expression and secretion have also been associated with poor prognosis and high metastatic potential.

Because MUC1 is a tumor-associated antigen, many strategies that employ MUC1 as a potential target of therapeutic cancer vaccines have been evaluated during the last 20 years for the use of MUC1 as a potential target for cancer vaccines. Clinical trials have tested proteins, peptides, adjuvants, carriers, ex vivo-cultured dendritic cells (DCs), lysates, DC fusions, liposomes, poxviruses, adenoviruses, yeast, and C-type lectins targeting DCs.

Most clinical trials using MUC1 as a target for immunotherapy have enrolled patients with advanced metastatic disease who were not able to achieve long-term complete responses. One factor in this outcome could be that the majority of these clinical trials focused on the VNTR domain to mount a humoral or cell-mediated immune response against MUC1. A significant amount of N-terminal subunits containing the VNTR domain, shed into the blood during tumor progression, could partially explain the lack of immune response against tumor cells expressing MUC1 on their surface.

MUC1-C is the C-terminal subunit of MUC1. After the cleavage of MUC1, despite the larger extracellular subunit, MUC1-C remains anchored to the plasma membrane by a single-pass (28 amino acids) transmembrane domain (TD). It has been shown that MUC1-C, and not MUC1, is the predominant form of the protein on several different tumor-cell lines and cancer specimens, probably due to shedding of the N-terminal subunit. Furthermore, MUC1-C is uniformly distributed over the entire surface of tumor cells, whereas the N-terminal subunit is clustered at 1 or 2 points, recalling the normal behavior of MUC1 on healthy epithelium. Importantly, it has been demonstrated that some tissue specimens may stain positive for the presence of MUC1-C but negative for the N-terminal subunit.

In the last few years, evidence has rapidly accumulated concerning the role of MUC1-C as an oncogene. The 72 amino acid residues of MUC1-CD have been associated with a remarkable range of intracellular signaling functions, involving interactions with several mitochondrial, cytoplasmic, plasma membrane, and nuclear components. MUC1-CD is a target for several kinases, such as the $\zeta$ chain-associated 70-kD protein kinase (ZAP-70), the $\delta$ isoform of protein kinase C (PKC$\delta$), glycogen synthase kinase 3$\beta$ (GSK-3$\beta$), and the tyrosine kinases c-Src and Lck. Phosphorylation of MUC1-CD also may occur in response to the activation of several cell-surface growth factor receptors, including fibroblast growth factor receptor-3, platelet-derived growth factor receptor, and ErbB family members. Besides phosphorylation, MUC1-CD also can directly bind several proteins and receptors such as $\beta$-catenin, estrogen receptor-$\alpha$, and heat-shock proteins. MUC1-C transfection is sufficient to induce transformation and confer oncogenic activities previously attributed to the full-length MUC1 protein, such as increased growth rate, anchorage-independent cell growth, and resistance to chemotherapy agents. MUC1-C signaling activated by c-Src has been involved in the disruption of both E-cadherin adherens junctions and integrin focal adhesions that stimulate cancer cell motility, invasion, and metastasis, suggesting a possible role for MUC1-C in epithelial-mesenchymal transition. It has also been demonstrated that specific intracellular MUC1 peptides are able to inhibit cancer progression. Finally, it has been shown that MUC1-C mediates the growth of human pluripotent stem cells, and its expression could be used as a marker to identify and isolate undifferentiated cells.

There is a desire to identify new specific cytotoxic T lymphocyte (CTL) epitopes and enhancer agonist peptides of MUC1-C.

BRIEF SUMMARY OF THE INVENTION

The invention provides an isolated peptide comprising an amino acid sequence selected from the group consisting of SEQ ID NO: 2, SEQ ID NO: 5, SEQ ID NO: 8, SEQ ID NO: 10, SEQ ID NO: 13, SEQ ID NO: 14, SEQ ID NO: 29, and SEQ ID NO: 32. The invention also provides an isolated peptide having no more than 20 amino acid residues and comprising SEQ ID NO: 3, SEQ ID NO: 6, SEQ ID NO: 9, SEQ ID NO: 11, SEQ ID NO: 15, SEQ ID NO: 26, or SEQ ID NO: 30.

In another aspect, the invention provides a nucleic acid encoding the peptide, a vector comprising the nucleic acid, a cell comprising the peptide, nucleic acid, or vector, and compositions thereof.

The invention also provides a method of enhancing an immune response against a MUC1-expressing cancer in a host comprising administering a therapeutically effective amount of a composition comprising the peptide, nucleic acid, vector, or cell to the host, wherein the immune response in the host is enhanced.

The invention further provides a method of inhibiting a MUC1-expressing cancer in a subject comprising (a) obtaining (isolating) lymphocytes from the subject, (b) stimulating the lymphocytes with a composition comprising the peptide, nucleic acid, vector, or cell to the host to generate cytotoxic T lymphocytes ex vivo, and (c) administering the cytotoxic T lymphocytes to the subject, wherein the MUC1-expressing cancer in the subject is inhibited.

The invention provides a method inhibiting a MUC1-expressing cancer in a subject comprising (a) obtaining (isolating) dendritic cells from the subject; (b) treating the dendritic cells with a composition comprising the peptide, nucleic acid, vector, or cell ex vivo; and (c) administering the treated dendritic cells to the subject, wherein the MUC1-expressing cancer in the subject is inhibited.

Additionally, the invention provides inhibiting a MUC1-expressing cancer in a subject comprising (a) obtaining peripheral blood mononuclear cells (PBMCs) from a subject suffering from cancer, (b) isolating dendritic cells from the PBMCs, (c) treating the dendritic cells with a composition comprising the peptide, nucleic acid, vector, or cell ex vivo, (d) activating the PBMCs with the treated dendritic cells ex vivo; and (e) administering the activated PBMCs to the subject, wherein the MUC1-expressing cancer in the subject is inhibited.

The invention further provides inhibiting a MUC1-expressing cancer in a subject comprising (a) obtaining peripheral blood mononuclear cells (PBMCs) from a subject suffering from cancer, (b) isolating dendritic cells from the PBMCs, (c) treating the dendritic cells with a composition comprising the peptide, nucleic acid, vector, or cell ex vivo, (d) activating the PBMCs with the treated dendritic cells ex vivo; (e) isolating T lymphocytes from the activated PBMCs ex vivo, and (e) administering the isolated T lymphocytes to the subject, wherein the MUC1-expressing cancer in the subject is inhibited.

The invention provides the use of adoptively transferred T cells stimulated in vitro with a composition comprising the peptide, nucleic acid, vector, or cell to inhibit a MUC1-expressing cancer in a subject.

BRIEF DESCRIPTION OF THE SEVERAL VIEWS OF THE DRAWING(S)

Figure 1B:
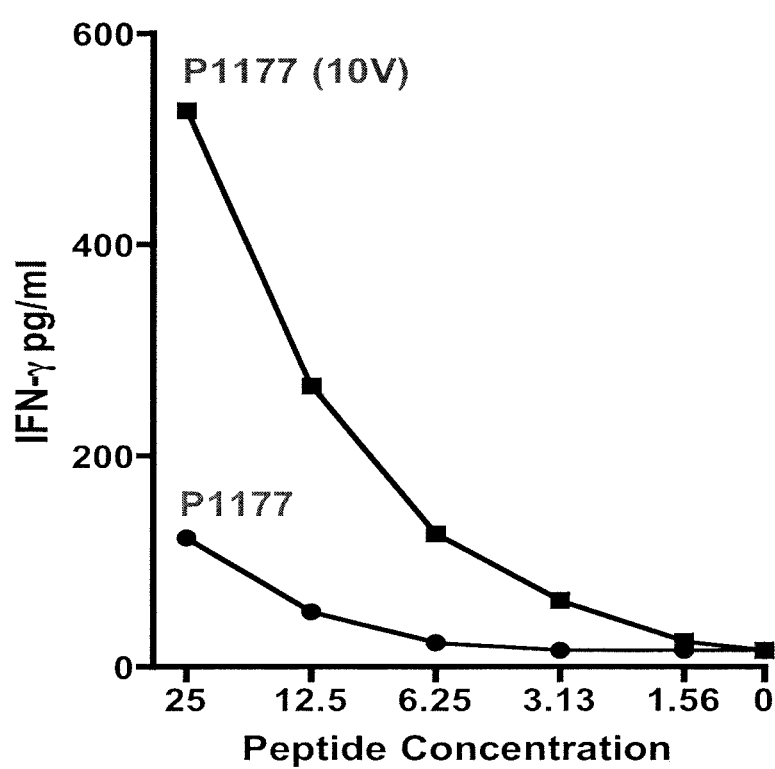
Figure 1C:
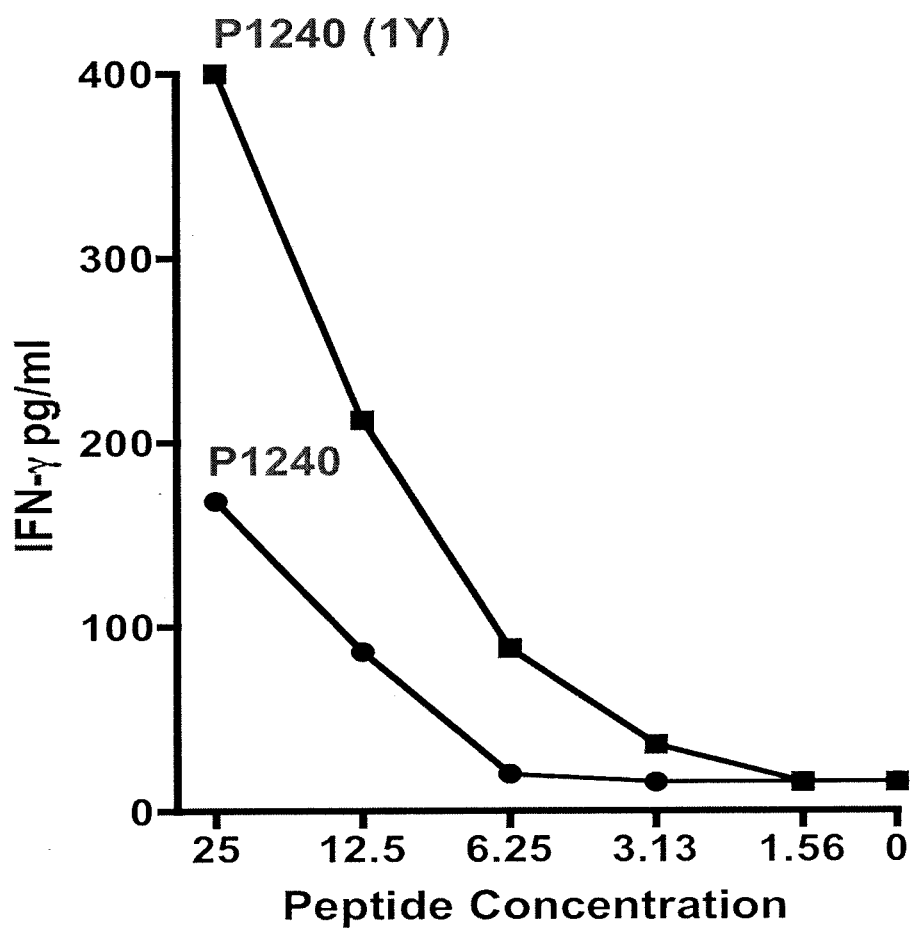

FIGS. 1A-C are graphs showing IFN-γ production by T-cell lines specific to native peptides and agonist peptides. IFN-γ (pg/mL) is represented on the y-axis and the peptide concentration (pg/mL) of each of (A) P1172 or P1172(1Y); (B) P1177 or P1177(10V); and (C) P1240 and P1240(1Y) is represented on the x-axis.

Figure 2A:
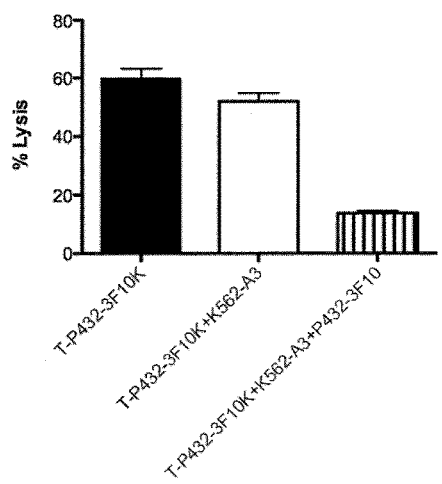
Figure 2B:
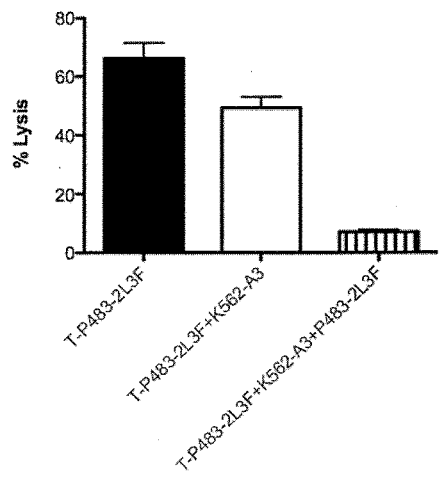

FIGS. 2A-B are graphs showing the peptide-specific T-cell line lysis of HLA-A3+, MUC1+ target cells using the T-cell lines T-P432-3F10K (A) and T-P483-2L3F (B). In each of the figures, the percent lysis is on the y-axis and on the x-axis is (a) the T-cell line alone, (b) the T-cell line plus K562-A3, and (c) the T-cell line plus K562-A3 plus the corresponding A3 peptide.

Figure 3:
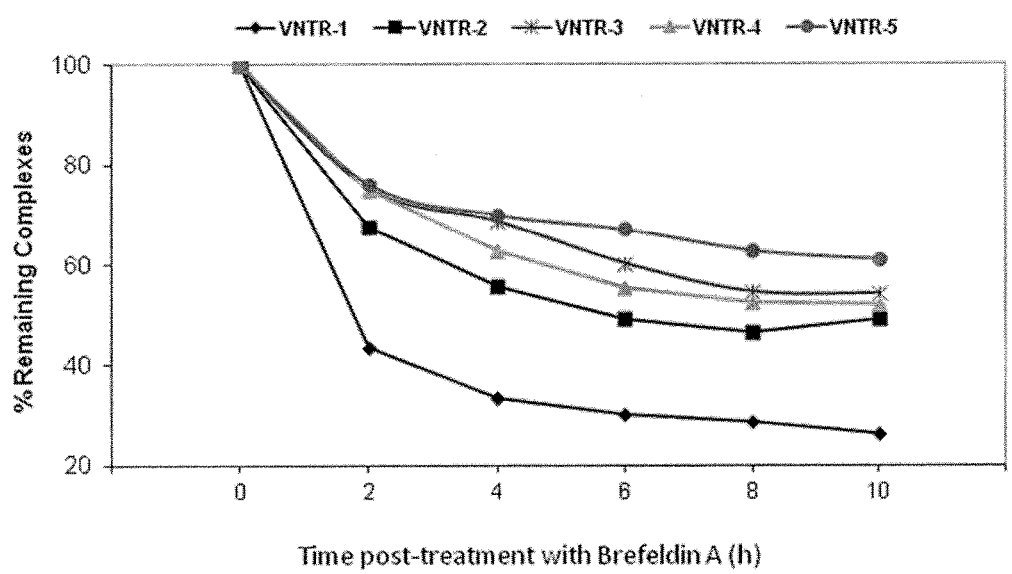

FIG. 3 is a graph showing the stability of the peptide/HLA-A2 complexes (for each of the VNTR-1, VNTR-2, VNTR-3, VNTR-4, and VNTR-5 peptides). The percentage of the remaining complexes is on the y-axis and the time in hours is on the x-axis.

DETAILED DESCRIPTION OF THE INVENTION

The invention provides peptides comprising a human cytolytic T lymphocyte (CTL) epitope from the human tumor-associated antigen (TAA) mucin 1 (MUC1) and analogs thereof, which can be used in vaccine prevention or therapy of cancer. In particular, the invention provides peptides comprising a human CTL epitope from MUC1-C and analogs thereof.

In a first embodiment, the inventive peptide comprises, consists essentially of or consists of the amino acid sequence of XLAIVYLIAL (SEQ ID NO: 3), wherein X can be any amino acid but is preferably alanine or tyrosine. When X of SEQ ID NO: 3 is alanine, the peptide corresponds to the CTL epitope at positions 1172-1181 of MUC1 (SEQ ID NO: 1). When X of SEQ ID NO: 3 is tyrosine, the peptide corresponds to an enhancer agonist epitope of MUC1 (SEQ ID NO: 2).

In second embodiment, the inventive peptide comprises, consists essentially of, or consists of the amino acid sequence of YLIALAVCQX (SEQ ID NO: 6), wherein X can be any amino acid but is preferably cysteine or valine. When X of SEQ ID NO: 6 is cysteine, the peptide corresponds to the CTL epitope at positions 1177-1186 of MUC1 (SEQ ID NO: 4). When X of SEQ ID NO: 6 is valine, the peptide corresponds to an enhancer agonist epitope of MUC1 (SEQ ID NO: 5).

In a third embodiment, the inventive peptide comprises, consists essentially of, or consists of the amino acid sequence of XLSYTNPAV (SEQ ID NO: 9), wherein X can be any amino acid but is preferably serine or tyrosine. When X of SEQ ID NO: 9 is serine, the peptide corresponds to the CTL epitope at positions 1240-1248 of MUC1 (SEQ ID NO: 7). When X of SEQ ID NO: 9 is tyrosine, the peptide corresponds to an enhancer agonist epitope of MUC1 (SEQ ID NO: 8).

In a forth embodiment, the inventive peptide comprises $ALX_1IVYLIAX_2$, (SEQ ID NO: 11), wherein $X_1$ and $X_2$ can be any amino acid but preferably $X_1$ is alanine or phenylalanine and $X_2$ is leucine or lysine. When $X_1$ of SEQ ID NO: 11 is alanine and $X_2$ of SEQ ID NO: 11 is leucine, the peptide corresponds to the CTL epitope at positions 1172-1181 of MUC1 (SEQ ID NO: 1). When $X_1$ of SEQ ID NO: 11 is phenylalanine and $X_2$ of SEQ ID NO: 11 is lysine, the peptide corresponds to an enhancer agonist epitope of MUC1 (SEQ ID NO: 10).

In a fifth embodiment, the inventive peptide comprises $SX_1X_2RSPYEK$ (SEQ ID NO: 15), wherein $X_1$ and $X_2$ can be any amino acid but preferably $X_1$ is threonine or leucine and $X_2$ is aspartic acid, tyrosine, or phenylalanine. When $X_1$ of SEQ ID NO: 15 is threonine and $X_2$ of SEQ ID NO: 15 is aspartic acid, the peptide corresponds to the CTL epitope at positions 1223-1231 of MUC1 (SEQ ID NO: 12). When $X_1$ of SEQ ID NO: 15 is leucine and $X_2$ of SEQ ID NO: 15 is tyrosine, the peptide corresponds to an enhancer agonist epitope of MUC1 (SEQ ID NO: 13). When $X_1$ of SEQ ID NO: 15 is leucine and $X_2$ of SEQ ID NO: 15 is phenylalanine, the peptide corresponds to an enhancer agonist epitope of MUC1 (SEQ ID NO: 14).

In a sixth embodiment, the inventive peptide comprises $X_1X_2APPAHX_3V$ (SEQ ID NO: 26), wherein $X_1$, $X_2$, and $X_3$ can be any amino acid but preferably $X_1$ is serine or tyrosine, $X_2$ is threonine or lysine, and $X_3$ is asparagine or glycine. When $X_1$, $X_2$, and $X_3$ of SEQ ID NO: 26 are serine, threonine, and asparagine, respectively, the peptide corresponds to a CTL epitope of the variable number of tandem repeats (VNTR) region of MUC1 (SEQ ID NO: 27). When $X_1$, $X_2$, and $X_3$ of SEQ ID NO: 26 are serine, threonine, and glycine, respectively, the peptide corresponds to a CTL epitope of the VNTR region of MUC1 (SEQ ID NO: 28). When $X_1$, $X_2$, and $X_3$ of SEQ ID NO: 26 are tyrosine, lysine, and glycine, respectively, the peptide corresponds to an enhancer agonist epitope of the VNTR region of MUC1 (SEQ ID NO: 29).

In a seventh embodiment, the inventive peptide comprises $X_1X_2$DTRPAPX$_3$ (SEQ ID NO: 30), wherein $X_1$, $X_2$, and $X_3$ can be any amino acid but preferably $X_1$ is alanine or tyrosine, $X_2$ is proline or leucine, and $X_3$ is glycine or valine. When $X_1$, $X_2$, and $X_3$ of SEQ ID NO: 30 are alanine, proline, and glycine, respectively, the peptide corresponds to a CTL epitope of the VNTR region of MUC1 (SEQ ID NO: 31). When $X_1$, $X_2$, and $X_3$ of SEQ ID NO: 30 are tyrosine, leucine, and valine, respectively, the peptide corresponds to an enhancer agonist epitope of the VNTR region of MUC1 (SEQ ID NO: 32).

The inventive peptide can comprise one of the amino acid sequences of SEQ ID NOs: 1-15 and 26-32 and one or more flanking residues. The flanking residues should be chosen so as not to interfere with the ability of the peptide to induce an immune response (e.g., CTL activity). Guidance for the selection of such residues is provided by the relevant sequence of the MUC1 itself. For instance, one can choose residues for use in the peptide that are identical to, or have properties similar to, the residues at the corresponding positions of the MUC1 protein (preferably human MUC1).

When the peptide comprises a CTL epitope present in the native MUC1 sequence (e.g., SEQ ID NO: 1, SEQ ID NO: 4, SEQ ID NO: 7, SEQ ID NO: 12, SEQ ID NO: 27, SEQ ID NO: 28, and SEQ ID NO: 31), the peptide desirably has no more than 20 (e.g., no more than 19, no more than 18, no more than 17, no more than 16, no more than 15, no more than 14, no more than 13, no more than 12, no more than 11, or no more than 10) amino acid residues. In one embodiment, the additional amino acid residues, if present, are from MUC1 (e.g., MUC1-N, MUC1-C, or VNTR region). In this regard, the inventive peptide can be a fragment of the MUC1 (e.g., MUC1-N, MUC1-C, or VNTR region) protein that comprises no more than 20 contiguous amino acids of the MUC1 (e.g., MUC1-N, MUC1-C, or VNTR region) protein, wherein the peptide comprises the amino acid sequence of SEQ ID NO: 1, SEQ ID NO: 4, SEQ ID NO: 7, SEQ ID NO: 12, SEQ ID NO: 27, SEQ ID NO: 28, and SEQ ID NO: 31. The additional amino acid residues of the MUC1 protein can be positioned at either end or both ends of the amino acid sequence of SEQ ID NO: 1, SEQ ID NO: 4, SEQ ID NO: 7, SEQ ID NO: 12, SEQ ID NO: 27, SEQ ID NO: 28, and SEQ ID NO: 31.

In particular, the inventive peptide can comprise no more than 11 (e.g., no more than 10, no more than 9, no more than 8, no more than 7, no more than 6, no more than 5, no more than 4, no more than 3, no more than 2, no more than 1, or 0) amino acid residues at the C terminus of the amino acid sequence of SEQ ID NO: 1, SEQ ID NO: 4, SEQ ID NO: 7, SEQ ID NO: 12, SEQ ID NO: 27, SEQ ID NO: 28, and SEQ ID NO: 31, and/or no more than 11 (e.g., no more than 10, no more than 9, no more than 8, no more than 7, no more than 6, no more than 5, no more than 4, no more than 3, no more than 2, no more than 1, or 0) amino acid residues at the N terminus of the amino acid sequence of SEQ ID NO: 1, SEQ ID NO: 4, SEQ ID NO: 7, SEQ ID NO: 12, SEQ ID NO: 27, SEQ ID NO: 28, and SEQ ID NO: 31, wherein the inventive peptide has no more than 20 amino acid residues in total.

When the peptide comprises an enhancer agonist epitope of MUC1 (e.g., SEQ ID NO: 2, SEQ ID NO: 5, SEQ ID NO: 8, SEQ ID NO: 10, SEQ ID NO: 13, SEQ ID NO: 14, SEQ ID NO: 29, or SEQ ID NO: 32), the peptide can be any suitable length. In one embodiment, the peptide has no more than 20 (e.g., no more than 19, no more than 18, no more than 17, no more than 16, no more than 15, no more than 14, no more than 13, no more than 12, no more than 11, or no more than 10) amino acid residues. The additional amino acid residues, if present, preferably are from the MUC1 (e.g., MUC1-C) protein or based on the sequence of MUC1 as described herein. The additional amino acid residues can be positioned at either end or both ends of the amino acid sequence of SEQ ID NO: 2, SEQ ID NO: 5, SEQ ID NO: 8, SEQ ID NO: 10, SEQ ID NO: 13, SEQ ID NO: 14, SEQ ID NO: 29, or SEQ ID NO: 32.

In another embodiment, the invention provides a polypeptide that comprises the MUC1 amino acid sequence or fragment thereof, wherein one or more of the corresponding amino acid residues have been replaced with one or more of the enhancer agonist epitopes of MUC1 (e.g., SEQ ID NO: 2, SEQ ID NO: 5, SEQ ID NO: 8, SEQ ID NO: 10, SEQ ID NO: 13, SEQ ID NO: 14, SEQ ID NO: 29, or SEQ ID NO: 32). For example, the polypeptide can comprises the full-length MUC1 amino acid sequence or fragment thereof, wherein the alanine at position 1172 has been replaced with tyrosine (corresponding to the enhancer agonist epitope of SEQ ID NO: 2).

The peptide can be prepared by any method, such as by synthesizing the peptide or by expressing a nucleic acid encoding an appropriate amino acid sequence in a cell and harvesting the peptide from the cell. A combination of such methods also can be used. Methods of de novo synthesizing peptides and methods of recombinantly producing peptides are known in the art (see, e.g., Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwood et al., Oxford University Press, Oxford, United Kingdom, 2000; Sambrook et al., *Molecular Cloning: A Laboratory Manual*, 3$^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994).

The invention also provides a nucleic acid encoding the peptide. The nucleic acid can comprise DNA or RNA, and can be single or double stranded. Furthermore, the nucleic acid can comprise nucleotide analogues or derivatives (e.g., inosine or phophorothioate nucleotides and the like). The nucleic acid can encode the peptide alone or as part of a fusion protein. The nucleic acid encoding the peptide can be provided as part of a construct comprising the nucleic acid and elements that enable delivery of the nucleic acid to a cell, and/or expression of the nucleic acid in a cell. Such elements include, for example, expression vectors, promoters, and transcription and/or translation sequences. Suitable vectors, promoters, transcription/translation sequences, and other elements, as well as methods of preparing such nucleic acids and constructs, are known in the art (e.g., Sambrook et al., supra; and Ausubel et al., supra).

The invention further provides a vector comprising the nucleic acid. Examples of suitable vectors include plasmids (e.g., DNA plasmids), yeast (e.g., *Saccharomyces*), and viral vectors, such as poxvirus, retrovirus, adenovirus, adeno-associated virus, herpes virus, polio virus, alphavirus, baculorvirus, and Sindbis virus. When the vector is a plasmid (e.g., DNA plasmid), the plasmid can be complexed with chitosan. Preferably, the vector is a poxvirus selected from the group consisting of orthopox, avipox, fowlpox, raccoon pox, rabbit pox, capripox (e.g., sheep pox), leporipox, and suipox (e.g., swinepox). Preferred examples of avipox viruses include fowlpox, pigeonpox, and canarypox, such as ALVAC. Preferred examples of orthopox viruses include vaccinia, modified vaccinia Ankara (MVA), Wyeth, NYVAC, TROYVAC, Dry-Vax, PDXVAC-TC (Schering-Plough Corporation), and derivatives thereof. For example, derivatives of the Wyeth strain include, but are not limited to, derivatives which lack a functional K1L gene.

When the vector is for administration to a host (e.g., human), the vector (e.g., poxvirus) preferably has a low replicative efficiency in a target cell (e.g., no more than about 1 progeny per cell or, more preferably, no more than 0.1 progeny per cell are produced). Replication efficiency can readily be determined empirically by determining the virus titer after infection of the target cell.

In addition to the nucleic acid encoding the peptide, the vector also can comprise gene(s) encoding one or more immunostimulatory/regulatory molecules, granulocyte macrophage colony stimulating factor (GM-CSF), cytokines, or other molecules that can enhance an immune response (e.g., additional tumor-associated antigens, such as prostate specific antigen (PSA) and carcinoembryonic antigen (CEA) or modified versions thereof such as CEA-6D). The nucleic acid encoding the peptide, as well as any other exogenous gene(s), preferably are inserted into a site or region (insertion region) in the vector (e.g., poxvirus) that does not affect virus viability of the resultant recombinant virus. Such regions can be readily identified by testing segments of virus DNA for regions that allow recombinant formation without seriously affecting virus viability of the recombinant virus.

The thymidine kinase (TK) gene is an insertion region that can readily be used and is present in many viruses. In particular, the TK gene has been found in all examined poxvirus genomes. Additional suitable insertion sites are described in International Patent Application Publication WO 2005/048957. For example, in fowlpox, insertion regions include, but are not limited to the BamHI J fragment, EcoRI-HindIII fragment, BamHI fragment, EcoRV-HindIII fragment, long unique sequence (LUS) insertion sites (e.g., FPV006/FPV007 and FPV254/FPV255), FP14 insertion site (FPV060/FPV061), and 43K insertion site (FPV107/FPV108). In vaccinia, insertion sites include, but are not limited to, 44/45, 49/50, and 124/125.

When the vector is a recombinant fowlpox virus comprising a nucleic acid encoding the peptide and/or other exogenous gene(s) (e.g., encoding one or more immunostimulatory/regulatory molecules), the nucleic acid encoding the peptide can be inserted in one region (e.g., the FP14 region), and the exogenous gene(s) can be inserted in another region (e.g., the BamHI J region).

The inventive vector can include suitable promoters and regulatory elements, such as a transcriptional regulatory element or an enhancer. When the vector is a poxvirus vector, poxvirus promoters can be used, including but not limited to the vaccinia 7.5K promoter, vaccinia 30K promoter, vaccinia 40K promoter, vaccinia 13 promoter, synthetic early/late (sE/L) promoter, 7.5 promoter, HH promoter, 11K promoter, and Pi promoter. While the promoters typically will be constitutive promoters, inducible promoters also can be used in the inventive vectors. Such inducible systems allow regulation of gene expression.

A cell comprising the peptide, nucleic acid encoding the peptide, or vector also is provided herein. Suitable cells include prokaryotic and eukaryotic cells, e.g., mammalian cells, yeast, fungi, and bacteria (such as E. coli). The cell can be in vitro, as is useful for research or for production of the peptide, or the cell can be in vivo. The cell can be a peptide-pulsed antigen presenting cell. Suitable antigen presenting cells include, but are not limited to, dendritic cells, B lymphocytes, monocytes, macrophages, and the like.

In one embodiment, the cell is dendritic cell. Dendritic cells of different maturation stages can be isolated based on the cell surface expression markers. For example, mature dendritic cells are less able to capture new proteins for presentation but are much better at stimulating resting T cells to grow and differentiate. Thus, mature dendritic cells can be of importance. Mature dendritic cells can be identified by their change in morphology and by the presence of various markers. Such markers include, but are not limited to, cell surface markers such as B7.2, CD40, CD11, and MHC class II. Alternatively, maturation can be identified by observing or measuring the production of pro-inflammatory cytokines.

Dendritic cells can be collected and analyzed using typical cytofluorography and cell sorting techniques and devices, such as a fluorescence-activated cell sorter (FACS). Antibodies specific to cell surface antigens of different stages of dendritic cell maturation are commercially available.

The peptide, nucleic acid, vector, or cell can be isolated. The term "isolated" as used herein encompasses compounds or compositions that have been removed from a biological environment (e.g., a cell, tissue, culture medium, body fluid, etc.) or otherwise increased in purity to any degree (e.g., isolated from a synthesis medium). Isolated compounds and compositions, thus, can be synthetic or naturally produced.

The peptide, nucleic acid, vector, or cell can be formulated as a composition (e.g., pharmaceutical composition) comprising the peptide, nucleic acid, vector, or cell and a carrier (e.g., a pharmaceutically or physiologically acceptable carrier). Furthermore, the peptide, nucleic acid, vector, cell, or composition of the invention can be used in the methods described herein alone or as part of a pharmaceutical formulation.

The composition (e.g., pharmaceutical composition) can comprise more than one peptide, nucleic acid, vector, or cell or composition of the invention. Alternatively, or in addition, the composition can comprise one or more other pharmaceutically active agents or drugs. Examples of such other pharmaceutically active agents or drugs that may be suitable for use in the pharmaceutical composition include anticancer agents (e.g., chemotherapeutic drugs), antibiotics, antiviral drugs, antifungal drugs, cyclophosphamide, and combinations thereof. Suitable anticancer agents include, without limitation, alkylating agents, nitrogen mustards, folate antagonists, purine antagonists, pyrimidine antagonists, spindle poisons, topoisomerase inhibitors, apoptosis inducing agents, angiogenesis inhibitors, podophyllotoxins, nitrosoureas, cisplatin, carboplatin, interferon, asparginase, tamoxifen, leuprolide, flutamide, megestrol, mitomycin, bleomycin, doxorubicin, irinotecan, taxol, geldanamycin (e.g., 17-AAG), and various anti-cancer peptides and antibodies known in the art.

The carrier can be any of those conventionally used and is limited only by physiochemical considerations, such as solubility and lack of reactivity with the active compound(s)

and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular peptide, nucleic acid, vector, cell, or composition thereof of the invention and other active agents or drugs used, as well as by the particular method used to administer the peptide, nucleic acid, vector, cell, or composition thereof.

The composition additionally or alternatively can comprise one or more immunostimulatory/regulatory molecules. Any suitable immunostimulatory/regulatory molecule can be used, such as interleukin (IL)-2, IL-4, IL-6, IL-12, interferon (IFN)-γ, tumor necrosis factor (TNF)-α, B7.1, B7.2, ICAM-1, LFA-3, CD70, RANTES, G-CSF, OX-40L, 41 BBL, anti-CTLA-4, and combinations thereof. Preferably, the composition comprises a combination of B7.1, ICAM-1, and LFA-3 (also referred to as TRICOM). The one or more immunostimulatory/regulatory molecules can be administered in the form of vector (e.g., a recombinant viral vector, such as a poxvirus vector) comprising a nucleic acid encoding one or more immunostimulatory/regulatory molecules. For example, the one or more immunostimulatory/regulatory molecules (e.g., IL-12) can be administered in the form of a DNA plasmid with or without chitosan. Alternatively, the one or more immunostimulatory/regulatory molecules can be administered as a protein (e.g., recombinant protein), such as a protein (e.g., recombinant IL-12) admixed with chitosan.

In one embodiment of the invention, the composition comprises a first recombinant vector comprising the nucleic acid encoding the inventive peptide and second recombinant vector comprising a nucleic acid encoding B7.1, ICAM-1, and LFA-3. In another embodiment, the nucleic acid encoding the inventive peptide and the nucleic acid encoding B7.1, ICAM-1, and LFA-3 are in the same recombinant vector. The first and/or second vectors additionally can comprise a nucleic acid encoding another tumor associated antigen (e.g., CEA), a modified version thereof (e.g., CEA-6D), or an epitope thereof.

The invention provides a method of transducing dendritic cells with the peptide, nucleic acid, vector, cell, or composition thereof, and optionally, immunostimulatory/regulatory molecules molecules, such as for example, B7-1, ICAM-1 and LFA-3. In one aspect of the invention, dendritic cells transduced with the peptide, nucleic acid, vector, cell, or composition thereof to the host generate an immune response, such as activation of a cytotoxic T cell response.

The invention provides methods of treating a subject suffering from or susceptible to a MUC1 tumor and/or enhancing an immune response against a MUC1-expressing cancer and/or inhibiting a MUC-1 expressing cancer. In a first embodiment, the inventive methods comprise administering a therapeutically effective amount of one or more of the peptide, nucleic acid, vector, cell, or composition thereof to a subject. The inventive peptide, nucleic acid, vector, cell, or composition thereof can be used to prevent the development of a MUC1-expressing cancer, particularly in an individual at higher risk to develop such cancer than other individuals, or to treat a patient afflicted with a MUC1-expressing cancer. The inventive peptide, nucleic acid, vector, cell, or composition thereof can be used to treat a subject with any stage MUC1-expressing cancer.

In a second embodiment, the inventive methods comprise obtaining (by isolating) dendritic cells from a subject, treating the dendritic cells with one or more of the therapeutically effective amount of the peptide, nucleic acid, vector, cell, or composition thereof, and administering the treated dendritic cells to the subject.

In a third embodiment, the inventive methods comprise (a) obtaining (isolating) peripheral blood mononuclear cells (PBMCs) from a subject, (b) isolating dendritic cells from the PBMCs, (c) treating the dendritic cells with one or more of the therapeutically effective amount of the peptide, nucleic acid, vector, cell, or composition thereof ex vivo, (d) activating the PBMCs with the treated dendritic cells ex vivo; and (e) administering the activated PBMCs to the subject.

In a fourth embodiment, the inventive methods comprise (a) obtaining (isolating) PBMCs from a subject, (b) isolating dendritic cells from the PBMCs, (c) treating the dendritic cells with one or more of the therapeutically effective amount of the peptide, nucleic acid, vector, cell, or composition thereof ex vivo, (d) activating the PBMCs with the treated dendritic cells ex vivo; and (e) administering the activated PBMCs to the subject.

In a fifth embodiment, the inventive methods comprise a method for inhibiting a MUC1-expressing cancer in a subject comprising (a) obtaining (isolating) PBMCs from a subject, (b) isolating dendritic cells from the PBMCs, (c) treating the dendritic cells with one or more of the therapeutically effective amount of the peptide, nucleic acid, vector, cell, or composition thereof ex vivo, (d) activating the PBMCs with the treated dendritic cells ex vivo; (e) isolating T lymphocytes from the activated PBMCs ex vivo, and (e) administering the isolated T lymphocytes to the subject.

The invention also provide the use of adoptively transferred T cells stimulated in vitro with one or more of the therapeutically effective amount of the peptide, nucleic acid, vector, cell, or composition thereof to inhibit a MUC1-expressing cancer in a subject.

The MUC1-expressing cancer can be any cancer expressing MUC1 including, but not limited to, human carcinomas (such as ovarian, breast, pancreatic, colorectal, lung, thyroid, gastric, head and neck, and prostate) and hematologic malignancies (multiple myeloma and some B-cell non-Hodgkin's lymphomas).

The peptide, nucleic acid, vector, cell, or composition thereof can be administered to the host by any method. For example, the peptide or nucleic acid encoding the peptide (e.g., as a vector) can be introduced into a cell (e.g., in a host) by any of various techniques, such as by contacting the cell with the peptide, the nucleic acid, or a composition comprising the nucleic acid as part of a construct, as described herein, that enables the delivery and expression of the nucleic acid. Specific protocols for introducing and expressing nucleic acids in cells are known in the art (see, e.g., Sambrook et al. (eds.), supra; and Ausubel et al., supra).

Suitable methods of administering peptides, nucleic acids, vectors, cells, and compositions to hosts (subjects) are known in the art. The host (subject) can be any suitable host, such as a mammal (e.g., a rodent, such as a mouse, rat, hamster, or guinea pig, rabbit, cat, dog, pig, goat, cow, horse, primate, or human).

For example, the peptide, nucleic acid, or vector (e.g., recombinant poxvirus) can be administered to a host by exposure of tumor cells to the peptide, nucleic acid, or vector ex vivo or by injection of the peptide, nucleic acid, or vector into the host. The peptide, nucleic acid, vector (e.g., recombinant poxvirus) or combination of vectors, cell, and composition can be directly administered (e.g., locally administered) by direct injection into the cancerous lesion or tumor or by topical application (e.g., with a pharmaceutically acceptable carrier).

The peptide, nucleic acid, vector, cell, or composition thereof can be administered alone or in combination with adjuvants, incorporated into liposomes (as described in, e.g., U.S. Pat. Nos. 5,643,599, 5,464,630, 5,059,421, and 4,885,172), with cytokines, with biological response modifiers (e.g., interferon, interleukin-2 (IL-2), and colony-stimulating factors (CSF, GM-CSF, and G-CSF), or other reagents in the art that are known to enhance immune response.

Examples of suitable adjuvants include alum, aluminum salts, aluminum phosphate, aluminum hydroxide, aluminum silica, calcium phosphate, incomplete Freund's adjuvant, QS21, MLP-A, and RIBI DETOX™.

A particularly preferred adjuvant for use in the invention is the cytokine GM-CSF. GM-CSF has been shown to be an effective vaccine adjuvant because it enhances antigen processing and presentation by dendritic cells. Experimental and clinical studies suggest that recombinant GM-CSF can boost host immunity directed at a variety of immunogens.

GM-CSF can be administered using a viral vector (e.g., poxvirus vector) or as an isolated protein in a pharmaceutical formulation. GM-CSF can be administered to the host before, during, or after the initial administration of the peptide, nucleic acid, vector, cell, or composition thereof to enhance the antigen-specific immune response in the host. For example, recombinant GM-CSF protein can be administered to the host on each day of vaccination with the peptide, nucleic acid, vector, cell, or composition thereof and for each of the following 3 days (i.e. a total of 4 days). Any suitable dose of GM-CSF can be used. For instance, 50-500 μg (e.g., 100 μg, 200 μg, 300 μs, 400 μg, and ranges thereof) of recombinant GM-CSF can be administered per day. The GM-CSF can be administered by any suitable method (e.g., subcutaneously) and, preferably, is administered at or near the site of the vaccination of a host with the peptide, nucleic acid, vector, cell, or composition thereof.

In one embodiment, the inventive peptide can be conjugated to helper peptides or to large carrier molecules to enhance the immunogenicity of the peptide. These molecules include, but are not limited to, influenza peptide, tetanus toxoid, tetanus toxoid CD4 epitope, *Pseudomonas* exotoxin A, poly-L-lysine, a lipid tail, endoplasmic reticulum (ER) signal sequence, and the like.

The inventive peptide also can be conjugated to an immunoglobulin molecule using art-accepted methods. The immunoglobulin molecule can be specific for a surface receptor present on tumor cells, but absent or in very low amounts on normal cells. The immunoglobulin also can be specific for a specific tissue (e.g., breast, ovarian, colon, or prostate tissue). Such a peptide-immunoglobulin conjugate allows for targeting of the peptide to a specific tissue and/or cell.

The peptide, nucleic acid, vector, cell, or composition thereof is administered to a host (e.g., mammal, such as a human) in an amount effective to generate a MUC1-specific immune response, preferably a cellular immune response. The efficacy of the peptide, nucleic acid, vector, or cell as an immunogen may be determined by in vivo or in vitro parameters as are known in the art. These parameters include but are not limited to antigen specific cytotoxicity assays, regression of tumors expressing MUC1 or MUC1 epitopes, inhibition of cancer cells expressing MUC1 or MUC1 epitopes, production of cytokines, and the like.

Any suitable dose of the peptide, nucleic acid, vector, or cell or composition thereof can be administered to a host. The appropriate dose will vary depending upon such factors as the host's age, weight, height, sex, general medical condition, previous medical history, disease progression, and tumor burden and can be determined by a clinician. For example, the peptide can be administered in a dose of about 0.05 mg to about 10 mg (e.g., 0.1 mg, 0.5 mg, 1 mg, 2 mg, 3 mg, 4 mg, 5 mg, 6 mg, 7 mg, 8 mg, 9 mg, and ranges thereof) per vaccination of the host (e.g., mammal, such as a human), and preferably about 0.1 mg to about 5 mg per vaccination. Several doses (e.g., 1, 2, 3, 4, 5, 6, or more) can be provided (e.g., over a period of weeks or months). In one embodiment a dose is provided every month for 3 months.

When the vector is a viral vector, a suitable dose can include about $1\times10^5$ to about $1\times10^{12}$ (e.g., $1\times10^6$, $1\times10^7$, $1\times10^8$, $1\times10^9$, $1\times10^{10}$, $1\times10^{11}$, and ranges thereof) plaque forming units (pfus), although a lower or higher dose can be administered to a host. For example, about $2\times10^8$ pfus can be administered (e.g., in a volume of about 0.5 mL).

The inventive cells (e.g., cytotoxic T cells) can be administered to a host in a dose of between about $1\times10^5$ and $2\times10^{11}$ (e.g., $1\times10^6$, $1\times10^7$, $1\times10^8$, $1\times10^9$, $1\times10^{10}$, and ranges thereof) cells per infusion. The cells can be administered in, for example, one to three (e.g., two) infusions. In addition to the administration of the cells, the host can be administered a biological response modifier, such as interleukin 2 (IL-2). When the cells to be administered are cytotoxic T cells, the administration of the cytotoxic T cells can be followed by the administration of the peptide, nucleic acid, vector, or composition thereof in order to prime the cytotoxic T cells to further expand the T cell number in vivo.

When the cells to be administered are dendritic cells, the amount of dendritic cells administered to the subject will vary depending on the condition of the subject and should be determined via consideration of all appropriate factors by the practitioner. Preferably, about $1\times10^6$ to about $1\times10^{12}$ (e.g., about $1\times10^7$, about $1\times10^8$, about $1\times10^9$, about $1\times10^{10}$, or about $1\times10^{11}$ including ranges of any of the cell numbers described herein) dendritic cells are utilized for adult humans. These amounts will vary depending on the age, weight, size, condition, sex of the subject, the type of tumor to be treated, the route of administration, whether the treatment is regional or systemic, and other factors. Those skilled in the art should be readily able to derive appropriate dosages and schedules of administration to suit the specific circumstance and needs of the subject.

The invention provides a method of generating peptide-specific cytotoxic T lymphocytes in vivo, ex vivo, or in vitro by stimulation of lymphocytes with an effective amount of the inventive peptide, nucleic acid, vector, or cell, alone or in a composition with one or more immunostimulatory/regulatory molecules and/or adjuvant or in a liposome formulation. The lymphocytes can be lymphocytes from any suitable source, e.g., peripheral blood, tumor tissues, lymph nodes, and effusions, such as pleural fluid or ascites fluid.

The MUC1 peptide specific cytotoxic T lymphocytes are immunoreactive with MUC1. Preferably, the cytotoxic T lymphocytes inhibit the occurrence of tumor cells and cancer and inhibit the growth of, or kill, tumor cells expressing MUC1 or epitopes thereof. The cytotoxic T lymphocytes, in addition to being antigen specific, can be MHC class I restricted. In one embodiment, the cytotoxic T lymphocytes are MHC class I HLA-A2 restricted. In another embodiment, the cytotoxic T lymphocytes are MHC class I HLA-A3 restricted. The cytotoxic T lymphocytes preferably have a CD8+ phenotype.

In one embodiment, lymphocytes are removed from the host and stimulated ex vivo with the peptide, nucleic acid, vector, cell, or composition thereof to generate cytotoxic T lymphocytes. The cytotoxic T lymphocytes can be administered to the host in order to enhance an immune response to cancer, thereby inhibiting the cancer. Accordingly, the invention provides a method of inhibiting cancer in a host comprising (a) obtaining lymphocytes (e.g., from the host), (b) stimulating the lymphocytes with the peptide, nucleic acid, vector, cell, or composition thereof to generate cytotoxic T lymphocytes, and (c) administering the cytotoxic T lymphocytes to the host, wherein the cancer is inhibited.

In another embodiment, lymphocytes within the host are stimulated by administration to the host of the peptide, nucleic acid, vector, cell, or composition thereof to generate cytotoxic T lymphocytes, which cytotoxic T lymphocytes enhance an immune response to cancer, thereby inhibiting the cancer.

The invention includes a prime and boost protocol. In particular, the protocol includes an initial "prime" with a composition comprising one or more recombinant vectors encoding the inventive peptide and optionally one or more immunostimulatory/regulatory molecules and/or other tumor-associated antigens (e.g., CEA), modified versions thereof, and immunogenic epitopes thereof, followed by one or preferably multiple "boosts" with a composition containing the inventive peptide or one or more poxvirus vectors encoding the inventive peptide and optionally one or more immunostimulatory/regulatory molecules and/or other tumor-associated antigens (e.g., CEA), modified versions thereof, and immunogenic epitopes thereof.

The initial priming vaccination can comprise one or more vectors. In one embodiment, a single vector (e.g., poxvirus vector) is used for delivery of the inventive peptide and one or more immunostimulatory/regulatory molecules and/or other tumor-associated antigens (e.g., CEA), modified versions thereof, and immunogenic epitopes thereof. In another embodiment, two or more vectors (e.g., poxvirus vectors) comprise the priming vaccination, which are administered simultaneously in a single injection.

The boosting vaccinations also can comprise one or more vectors (e.g., poxvirus vectors). In one embodiment, a single vector is used for delivery of the inventive peptide and the one or more immunostimulatory/regulatory molecules and/or other tumor-associated antigens (e.g., CEA), modified versions thereof, and immunogenic epitopes thereof of the boosting vaccination. In another embodiment, two or more vectors comprise the boosting vaccination, which are administered simultaneously in a single injection.

Different vectors (e.g., poxvirus vectors) can be used to provide a heterologous prime/boost protocol using vectors carrying different sets of therapeutic molecules for inoculations at different time intervals. For example, in one heterologous prime/boost combination, a first orthopox vector composition is used to prime, and a second avipox vector composition is used to boost.

The schedule for administration of the vectors (e.g., poxvirus vectors) typically involves repeated administration of the boosting vector. The boosting vector can be administered 1-3 times (e.g., 1, 2, or 3 times) at any suitable time period (e.g., every 2-4 weeks) for any suitable length of time (e.g., 6-12 weeks for a total of at least 5-15 boosting vaccinations). For example, the primary vaccination can comprise a recombinant vaccinia or MVA vector followed by multiple booster vaccinations with an avipox vector. In a particular embodiment, the host receives one vaccination with the priming vector, followed every 2 weeks thereafter with the boosting vector for 6 boosts, followed by every 4 weeks thereafter with the boosting vector, and continuing with the boosting vector for a period of time dependent on disease progression.

The invention further provides a kit that has at least a first recombinant vector (e.g., poxvirus vector) that has incorporated into its genome or portion thereof a nucleic acid encoding the inventive peptide in a pharmaceutically acceptable carrier. The first recombinant vector (e.g., poxvirus vectors) also can comprise one or more nucleic acids encoding one or more immunostimulatory/regulatory molecules and/or other tumor-associated antigens (e.g., CEA), modified versions thereof, and immunogenic epitopes thereof. In addition to the first recombinant vector, the kit can have a second recombinant vector that comprises one or more nucleic acids encoding one or more immunostimulatory/regulatory molecules and/or other tumor-associated antigens (e.g., CEA), modified versions thereof, and immunogenic epitopes thereof in a pharmaceutically acceptable carrier. The kit further provides containers, injection needles, and instructions on how to use the kit. In another embodiment, the kit further provides an adjuvant such as GM-CSF and/or instructions for use of a commercially available adjuvant with the kit components.

The peptide, nucleic acid, vector, cell, or composition thereof can be administered to a host by various routes including, but not limited to, subcutaneous, intramuscular, intradermal, intraperitoneal, intravenous, and intratumoral. When multiple administrations are given, the administrations can be at one or more sites in a host.

Administration of the peptide, nucleic acid, vector, cell, or composition thereof can be "prophylactic" or "therapeutic." When provided prophylactically, the peptide, nucleic acid, vector, cell, or composition thereof is provided in advance of tumor formation to allow the host's immune system to fight against a tumor that the host is susceptible of developing. For example, hosts with hereditary cancer susceptibility are a preferred group of patients treated with such prophylactic immunization. The prophylactic administration of the peptide, nucleic acid, vector, cell, or composition thereof prevents, ameliorates, or delays the MUC1-expressing cancer. When provided therapeutically, the peptide, nucleic acid, vector, cell, or composition thereof is provided at or after the diagnosis of the MUC1-expressing cancer.

When the host has already been diagnosed with the MUC1-expressing cancer or metastatic cancer, the peptide, nucleic acid, vector, cell, or composition thereof can be administered in conjunction with other therapeutic treatments such as chemotherapy or radiation.

In a preferred embodiment, the administration of the peptide, nucleic acid, vector, cell, or composition thereof to a host results in a host cell expressing the inventive peptide and optionally one or more immunostimulatory/regulatory molecules and/or other tumor-associated antigens (e.g., CEA), modified versions thereof, and immunogenic epitopes thereof that were co-administered. The inventive peptide (i.e., MUC1 antigen) can be expressed at the cell surface of the infected host cell. The one or more immunostimulatory/regulatory molecules and/or other tumor-associated antigens (e.g., CEA), modified versions thereof, and immunogenic epitopes thereof can be expressed at the cell surface or may be actively secreted by the host cell. The expression of both the MUC1 antigen and the immunostimulatory/regulatory molecule provides the necessary MHC restricted peptide to specific T cells and the appropriate signal to the T cells to aid in antigen recognition and proliferation or clonal expansion of antigen specific T cells. The overall result is an upregulation of the immune system. Preferably, the upregulation of the immune response is an increase in antigen specific T-helper lymphocytes and/or cytotoxic lymphocytes, which are able to kill or inhibit the growth of a cancer (e.g., breast cancer, ovarian cancer, colon cancer, lung cancer, thyroid cancer, gastric cancer, head and neck cancer, or prostate cancer) cell.

There are a variety of suitable formulations of the pharmaceutical composition for the inventive methods. The following formulations for parenteral, subcutaneous, intravenous, intramuscular, and intraperitoneal administration are exemplary and are in no way limiting. One skilled in the art will appreciate that these routes of administering the peptide, nucleic acid, vector, cell, or composition of the invention are known, and, although more than one route can be used to administer a particular compound, a particular route can provide a more immediate and more effective response than another route.

Injectable formulations are among those formulations that are preferred in accordance with the present invention. The requirements for effective pharmaceutical carriers for injectable compositions are well-known to those of ordinary skill in the art (see, e.g., Pharmaceutics and Pharmacy Practice, J.B. Lippincott Company, Philadelphia, Pa., Banker and Chalmers, eds., pages 238-250 (1982), and ASHP Handbook on Injectable Drugs, Toissel, 4th ed., pages 622-630 (1986)).

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The peptide, nucleic acid, vector, cell, or composition thereof can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethylene glycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, and synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-b-aminopropionates, and 2-alkyl-imidazoline quaternary ammonium salts, and (e) mixtures thereof.

Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

The following examples further illustrate the invention but, of course, should not be construed as in any way limiting its scope.

Example 1

The following materials and methods were used for the experiments discussed in Examples 2-5.

Cell Cultures

The MCF-7 human breast adenocarcinoma cell line (HLA-A2$^+$/MUC1$^+$), the CF-PAC-1 human pancreatic adenocarcinoma cell line (HLA-A2$^+$/MUC1$^+$), the SK-Mel-24 melanoma cell line (HLA-A2$^+$/MUC1$^-$), and the ASPC-1 human pancreatic adenocarcinoma cell line (HLA-A27MUC1$^±$) were purchased from American Type Culture Collection (Manassas, Va.) and maintained in DMEM complete medium (Mediatech, Inc., Manassas, Va.) supplemented with 10% fetal bovine serum, 2 mM glutamine, 100 units/mL penicillin, 100 µg/mL streptomycin, 0.5 µg/mL amphotericin B (Mediatech, Inc.), and 0.01 µg/mL human recombinant insulin (Invitrogen Life Technologies, Inc., Carlsbad, Calif.). All cultures were *Mycoplasma*-free. The K562 human chronic myelogenous leukemia cell line (Anderson et al., *J. Immunol.*, 151: 3407-3419 (1993)) expressing HLA-A*0201 (K562/A*0201) (Storkus et al., *J. Immunol.*, 138: 1657-1659 (1987)) was obtained from C. Britten (Johannes Gutenberg University of Mainz, Mainz, Germany) and cultured in RPMI-1640 complete medium supplemented with 10% heat-inactivated fetal bovine serum, 2 mM glutamine, 100 units/mL penicillin, 100 µg/mL streptomycin, 0.5 µg/mL, and 0.7 mg/mL G418. The 174CEM-T2 cell line (T2) transport deletion mutant (Hogan et al., *J. Exp. Med.*, 168: 725-736 (1988)) was provided by Dr. Peter Cresswell (Yale University School of Medicine, New Haven, Conn.). C1R-A2 cells and T2 cells were *Mycoplasma*-free and were maintained in RPMI-1640 complete medium and Iscove's modified Dulbecco's complete medium (Mediatech, Inc.), respectively.

Peptides

The amino acid sequence of MUC1-C was scanned for matches to consensus motifs for HLA-A2-binding using the computer algorithm from the BioInformatics and Molecule Analysis Section of NIH (Parker et al., *J. Immunol.*, 152: 163-175 (1994)), which ranks potential MHC-binding peptides according to the predictive half-time dissociation of peptide/MHC complexes. American Peptide Company (Sunnyvale, Calif.) synthesized seven 9-mer or 10-mer peptides and analogs thereof from MUC1-C. The purity of the peptides was >90%.

Flow Cytometric Analysis

Single-color flow cytometric analysis has been previously described in Guadagni et al., *Cancer Res.*, 50: 6248-6255 (1990). Briefly, cells were washed 3 times with cold Ca2+- and Mg2+-free Dulbecco's phosphate-buffered saline (PBS), and then stained for 1 h at 4° C. using FITC-conjugated monoclonal antibodies anti-HLA-A2,28 (One Lambda, Inc., Canoga Park, Calif.), anti-CD3, anti-CD4, and anti-CD8 (BD Biosciences, San Jose, Calif.). Mouse IgG2a, k FITC (BD Biosciences) was used as isotype control. The cells were then washed 3 times with cold Ca2+- and Mg2+-free PBS, resuspended in the same buffer, and immediately analyzed using a FACScan (Becton Dickinson, Franklin Lakes, N.J.) and CellQuest software (BD Biosciences). Results were generated from data gathered from 10,000 live cells and expressed as percent-positive cells and mean fluorescence intensity (MFI). The MFI value was collected in log scale and used to express levels of fluorescence determined by measuring the average for all cells in the fluorescence dot plot.

The procedure for dual-color flow cytometric analysis was similar to that for single-color analysis with the following exceptions. Dendritic cells were analyzed using the following antibody combinations: anti-MHC class II FITC/anti-CD11c APC; anti-class I FITC/anti-CD80 phycoerythrin (PE); anti-class I FITC/anti-CD83 PE; anti-class I FITC/anti-CD86 PE; anti-class I FITC/anti-class II PE; anti-class I FITC/anti-CD58 PE; anti-class I FITC/anti-CD54 PE. Mouse IgG1, k FITC, mouse IgG1, k PE, and mouse IgG2a, k FITC were used as isotype controls; >96% of DCs were CD11c+ and MHC class II+. Antibody to MHC class II was purchased from Serotec (Oxford, UK) and other antibodies were purchased from BD Biosciences.

Peptide Binding to HLA-A2

Binding of P1172, P1177, P1240, and their analogs to HLA-A2 molecules was evaluated by the upregulation of HLA-A2 expression on T2A2 cells, as demonstrated by flow cytometry (Nijman et al., *Eur. J. Immunol.*, 23: 1215-1219 (1993)).

Culture of DCs from PBMCs

Peripheral blood mononuclear cells (PBMCs) were obtained from heparinized blood from HLA-A2+ patients enrolled in the PANVAC-VF clinical trial. PBMCs were separated using lymphocyte separation medium gradient (MP Biomedicals, Aurora, Ohio) according to the manufacturer's instructions (Boyum, *Scand. J. Clin. Lab. Invest. Suppl.*, 97: 51-76 (1968)). DCs were prepared from PBMCs, as described in Sallusto et al., *J. Exp. Med.*, 179: 1109-1118 (1994)).

Generation of T-Cell Lines

MUC1-C-specific CTLs were generated by a modification of the protocol described by Tsang et al., *J. Natl. Cancer Inst.*, 87: 982-990 (1995). P1172-, P1172(1Y)-, P1177-, and P1177(10V)-specific T-cell lines were generated from 2 colon carcinoma patients vaccinated with a MUC1-CEA-based vaccine. P1240- and P1240(1Y)-specific T-cell lines were generated from an ovarian carcinoma patient and a breast carcinoma patient who also received the MUC1-CEA-based vaccine. CD40L or yeast-matured autologous DCs, generated as previously described, were used as antigen-presenting cells (APCs). PBMCs obtained on day 70 post-vaccination were added to the APCs and pulsed with 12.5 µg/mL of the corresponding peptide at an effector:APC ratio of 10:1. Autologous DCs were used as APCs for 3 in vitro stimulation (IVS) cycles. Irradiated (23,000 rads) autologous EBV-transformed B cells were used as APCs after the third IVS cycle. For restimulation with EBV-transformed B cells, peptides at a concentration of 12.5 ng/mL were used to pulse the autologous EBV-transformed B cells at an effector:APC ratio of 1:3. Cultures were incubated for 3 days at 37° C. in a humidified atmosphere containing 5% $CO_2$. The cultures were then supplemented with recombinant human IL-2 at a concentration of 20 U/mL for 7 days; the IL-2-containing medium was replenished every 3 days. The 3-day incubation with peptide and 7-day IL-2 supplement constituted one IVS cycle.

Tetramer Staining

Streptavidin-PE-labeled P1172(1Y)/HLA-A*0201 tetramer, PE-labeled P1177(10V)/HLA-A*0201 tetramer, PE-labeled P1240/HLA-A*0201 tetramer, and PE-labeled P1240(1Y)/HLA-A*0201 tetramer were prepared by the Tetramer Core Facility (Atlanta, Ga.). PE-labeled HIV gag (SEQ ID NO: 25)/HLA-A*0201 tetramer was obtained from Beckman Coulter (Fullerton, Calif.) and used as a negative control. PBMCs (1×10$^6$) were stained with 1 µL of tetramer and anti-CD8-FITC antibody (BD Biosciences) for 30 min at room temperature in the dark, washed twice with FACS buffer, and analyzed using a FACScan and CellQuest software. Results were generated from data gathered from 100,000 cells.

Cytotoxic Assay

Target cells were labeled with 50 µCi of $^{111}$In-labeled oxyquinoline (Medi-Physics Inc., Arlington, Ill.) for 15 min at room temperature. Target cells (3×10$^3$) in 100 µL, of RPMI-1640 complete medium were added to each of 96 wells in flat-bottomed assay plates. Effector cells were suspended in 100 µL of RPMI-1640 complete medium supplemented with 10% pooled human AB serum and added to the target cells. The plates were then incubated at 37° C. in 5% $CO_2$ for 4 or 16 h. Supernatant was harvested for gamma counting with the use of harvester frames (Skatron, Inc., Sterling, Va.). Determinations were carried out in triplicate, and standard deviations were calculated. Specific lysis was calculated according to the following formula (all values in cpm):

$$\% \text{ lysis} = \frac{\text{Observed release} - \text{spontaneous release}}{\text{Total release} - \text{spontaneous release}} \times 100$$

Spontaneous release was determined from wells to which 100 µL of RPMI-1640 complete medium were added. Total releasable radioactivity was obtained after treatment of targets with 2.5% Triton X-100.

Detection of Cytokines

Supernatants of T cells stimulated for 24 h with peptide-pulsed autologous DCs or autologous EBV-transformed B cells in IL-2-free medium at various peptide concentrations were screened for secretion of IFN-γ by ELISA kit (BioSource International, Camarillo, Calif.). Results were expressed in pg/mL.

Statistical Analysis

Statistical significance was calculated using a 2-tailed paired Student's t-test and StatView software (Abacus Concepts, Berkeley, Calif.).

Example 2

This example demonstrates the determination of CTL epitopes of MUC1-C subunit and analogs thereof.

The primary amino acid sequence of the MUC1-C subunit (corresponding to residues 1098 to 1254 of the MUC1 sequence) was analyzed for consensus motifs for HLA-A2 binding peptides. Two 10-mer peptides (designated P1172 and P1177) and one 9-mer peptide (designated P1240) were identified and synthesized (see Table 1). Three analogs of native epitopes P1172, P1177, and P1240 (P1172(1Y), P1177(10V), and P1240(1Y), respectively) were generated by a single amino acid substitution at the amino acid residues at positions 1 and 10. Each of the analogs had a predicted higher affinity for HLA-A2 molecules than the corresponding native epitopes.

A peptide with a high affinity for HLA-A2 molecules (NGEP P703) (Cereda et al., *Cancer Immunol. Immunother.*, 59: 63-71 (2010)) and a specific HLA-A3 peptide (CAP-7) were used in the assays as positive and negative controls, respectively.

cancer patient (patient 2) vaccinated with recombinant vaccinia-CEA-MUC1-TRICOM and recombinant fowlpox-CEA-MUC1-TRICOM were used to establish specific CD8+ cell lines against these MUC1-C native and agonist peptides. The T-cell lines generated using P1172, P1172(1Y), P1177, and P1177(10V) from patient 1 were designated T-1-P1172, T-1-1172(1Y), T-1-P1177, and T-1-P1177(10V), respectively. The T-cell lines generated from patient 2 using P1240 and P1240(1Y) were designated T-2-P1240 and T-2-P1240(1Y), respectively.

To evaluate the specificity of these T-cell lines, an IFN-γ release assay was performed using irradiated autologous B cells pulsed with the corresponding peptide. T cells were stimulated with irradiated autologous B cells pulsed with corresponding peptide at an APC:T cell ratio of 2:1. T cells were used at a concentration of $5\times10^5$/mL. 24 hour culture supernatants were collected and screened for secretion of

TABLE 1

Binding of MUC1 peptides to HLA-A2 molecules.

| Peptide* | Amino Acid Sequence | SEQ ID NO: | Amino Acid Position in MUC1 | T2 Binding# |
|---|---|---|---|---|
| P1172 | ALAIVYLIAL | 1 | 1172-1181 | 248.6 |
| P1172(1Y) | YLAIVYLIAL | 2 | 1172-1181 | 245.1 |
| P1177 | YLIALAVCQC | 4 | 1177-1186 | 211.2 |
| P1177(10V) | YLIALAVCQV | 5 | 1177-1186 | 299.1 |
| P1240 | SLSYTNPAV | 7 | 1240-1248 | 325.8 |
| P1240(1Y) | YLSYTNPAV | 8 | 1240-1248 | 342.1 |
| NGEP (P703) (positive control) | GLFDEYLEMV | 16 | NA | 481.93 |
| CAP-7 (negative control) | HLFGYSWYK | 17 | NA | 109.1 |

*Peptides were used at a concentration of 12.5 µg/mL.
Results expressed as mean fluorescence intensity (MFI).
NGEP (P703) peptide is an HLA-A2-binding peptide.
CAP-7 peptide is an HLA-A3-binding CEA peptide P1177, P1172, and P1240 showed a greater affinity for HLA-A2 molecules compared to the negative control. Analog peptides P1177(10V) and P1240(1Y) showed a greater affinity for HLA-A2 molecules compared to the corresponding native peptides P1177 and P1240.

The stability of the peptide/HLA-A2 complexes of the analogs and native peptides were analyzed by determining the percentage of the remaining complexes on HLA-A2 molecules at different time points (0, 2, 4, 6, 8, and 10 h). The analog peptide P1177(10V) demonstrated a greater avidity for class I molecules than the native peptide P1177 at each time point. No differences were seen between P1172(1Y) and P1172 and P1240(1Y) and P1240 in terms of half-time of dissociation.

Example 3

This example demonstrates the further characterization of CTL epitopes of the MUC1-C subunit and analogs thereof.

The immunogenicity of P1172, P1177, P1240, and their corresponding analogs was further investigated by evaluating their ability to generate specific CTLs in vitro. PBMCs from a colon carcinoma patient (patient 1) and a breast IFN-γ. T-1-P1172(1Y), T-1-P1177(10V), and T-2-P1240(1Y) cell lines produced higher levels of IFN-γ compared to T-cell lines generated using corresponding native peptides (Table 2).

TABLE 2

IFN-γ production by MUC1-C-specific T-cell lines stimulated with peptide-pulsed B cells.

| T cell line | Peptide | IFN-γ (pg/mL) |
|---|---|---|
| T-1-P1172 | P1172 | 158.3 |
| T-1-P1172(1Y) | P1172(1Y) | 605.0 |
| T-1-P1177 | P1177 | 666.4 |
| T-1-P1177(10V) | P1177(10V) | >1,000 |
| T-4-P1240 | P1240 | 437.3 |
| T-4-P1240(1Y) | P1240(1Y) | >1,000 |

Studies were then conducted to compare the ability of the native peptides and the agonist peptides, at various concentrations, to activate the agonist peptide-specific T cells. At each concentration of peptide, pulsing APCs with the agonist peptides P1172(1 Y), P1177(10V), and P1240(1Y) led to the greatest level of IFN-γ production by the agonist peptide-specific T-cell line, compared with the native peptides P1172, P1177, and P1240 (see FIG. 1 A-C).

An additional T-cell line was then established from the PBMCs of another patient (patient 3) with colon cancer from the same clinical trial described above, using P1177 and P1177(10V), designated T-3-P1177 and T-3-P1177(10V), respectively. T-3-P1177(10V) produced higher levels of IFN-γ than T-3-P1177 (>1,000 pg/mL vs. 456 pg/mL).

Example 4

This example demonstrates the immunogenicity of the MUC1 CTL epitopes and enhancer analog peptides in cancer patients.

The frequency of MUC1-C-specific CD8$^+$ T cells in the T-cell lines T-1-P1172, T-1-1172(1Y), T-1-P1177, T-1-P1177(10V), T-2-P1240, and T-2-P1240(1Y) was investigated using P1172(1Y)/HLA-A*0201 tetramer, P1177 (10V)/HLA-A*0201 tetramer, P1240(1Y)/HLA-A*0201 tetramer, and anti-CD8 antibody. A higher frequency of MUC1-C-specific CD8$^+$ T cells was generated in the agonist epitope-specific T-cell lines T-1-P1172(1Y), T-3-P1177 (10V), and T-2-P1240(1Y) compared to the T-cell lines generated using the corresponding native peptide (6.38% vs. 1.53%, 6.18% vs. 3.53%, and 6.6% vs. 1.6%, respectively).

These T-cell lines were then tested for cytotoxic activity against a MUC1$^+$/HLA-A2$^+$ breast carcinoma cell line (MCF-7) and a MUC1$^+$/HLA-A2$^+$ pancreatic cancer cell line (CF-PAC-1). A MUC1$^-$/HLA-A2$^+$ melanoma cell line (SK-MEL-24) and a MUC1$^+$/HLA-A2$^-$ pancreatic cancer cell line (ASPC-1) were used as negative controls. HLA-A2 and MUC1-C expression of these tumor cell lines was evaluated by flow cytometry (see Table 3).

TABLE 3

Expression of MUC1 and HLA-A2 in established human tumor cell lines.

| Tumor cell lines | MUC1 expression* | HLA-A2 expression* |
| --- | --- | --- |
| MCF-1 | 48.4 (363.8) | 85.9 (36.8) |
| CF-PAC-1 | 75.6 (120.7) | 99.9 (192.3) |
| ASPC-1 | 56.6 (86.7) | Negative |
| SK-MEL-24 | 2.9 (100.7) | 99.7 (466.6) |

*Values expressed as percent positive cells (MFI).

A 16 hour $^{111}$In release assay was performed using MUC1-C epitope-specific T-cell lines. MCF-7 cells were lysed by the agonist epitope-specific T-cell line to a greater degree than the T-cell line specific to the corresponding native epitope. As expected, no lysis was observed against SK-MEL-24 cells (see Table 4).

TABLE 4

Lysis of MUC1$^+$ tumor cells by MUC1-C agonist T-cell lines and T-cell lines generated with native epitopes.

| T cell line | E:T ratio | MCF-7 (HLA-A2$^+$/MUC-1$^+$)# | SK-MEL (HLA-A2$^+$/MUC-1$^-$)# |
| --- | --- | --- | --- |
| T-1-P1172 | 50:1 | 26.4 (2.72) | 8.0 (2.1) |
|  | 25:1 | 3.9 (1.78) | ND |
| T-1-P1172(1Y) | 50:1 | 40.7 (10.5)* | 0 |
|  | 25:1 | 25.5 (3.40)* | ND |
| T-1-P177 | 50:1 | 53.6 (6.34) | 4.6 (0.86) |
|  | 25:1 | 38.5 (0.69) | ND |
| T-1-P1177(10V) | 50:1 | 54.4 (2.98) | 0 |
|  | 25:1 | 46.2 (3.22)* | ND |
| T-4-P1240 | 50:1 | 9.2 (1.11) | ND |
|  | 25:1 | 8.4 (0.21) | 0.8 (0.12) |
| T-4-P1240(1Y) | 50:1 | 25.9 (2.1)* | ND |
|  | 25:1 | 20.8 (1.52)* | 1.3 (0.47) |

*p < 0.01 by t-test of agonist vs. native epitopes.
Results are expressed as percent specific lysis (standard deviation).
ND = not done Example 5

This example demonstrates the specificity and HLA-A2 restriction of CTL cytolysis of the T cell lines generated using the inventive peptides.

T-1-P1177(10V) and T-2-P1240(1Y) cells were selected because the cell lines produced high levels of IFN-γ, a high percentage of tetramer$^+$ T cells, and increased tumor-cell killing.

To confirm the specificity and HLA-A2 restriction of CTL cytolysis, T-1-P1177(10V) and T-2-P1240(1Y) cells were used in a cold target inhibition assay, with CF-PAC-1 cells as targets. $^{111}$In-labeled CF-PAC-1 cells and unlabeled K562/A2.1 cells were used at 1:10. K562/A2.1 cells were incubated 2 hours with or without peptide (25 µg/mL).

The addition of P1177(10V) and P1240(1Y) peptide-pulsed unlabeled K562/A2.1 cells decreased the CTL activity of T-1-P1177(10V) and T-2-P1240(1Y) cells against CF-PAC-1 controls from 21.1% to 4.0% lysis and from 13.5% to 1.7% lysis, respectively, at a 25:1 effector:target ratio (Table 5).

TABLE 5

Inhibition of lysis of CF-PAC-1 by MUC1-C-specific T-cell lines.

| Target Cells | |
| --- | --- |
|  | MUC1-C agonist-specific T cell (T-4-1777-10V)# |
| CF-PAC-1 | 21.2 (5.2) |
| CF-PAC-1 + K562/A2.1 | 16.9 (0.8) |
| CF-PAC-1 + K562/A2.1 + P1177(10V) | 4.0 (1.5)* |
|  | MUC1-C agonist-specific T cell (T-4-1240-1Y)# |
| CF-PAC-1 | 13.5 (5.1) |
| CF-PAC-1 + K562/A2.1 | 11.9 (2.3) |
| CF-PAC-1 + K562/A2.1 + P1240(1Y) | 1.7 (1.2)* |

*p < 0.01 by t-test of lysis with or without peptide.
Results are expressed as percent specific lysis at 25:1 E:T ratio (SD).

Antibody-blocking experiments were performed to determine whether the lysis was HLA-A2-restricted. In a 16 hour $^{111}$In release assay, CF-PAC-1 cells were incubated for 1 hour in medium containing no antibody, UPC-10 (10 µg/mL), or anti-HLA-A2 (10 µg/mL). The CTL activity of T-1-P1177(10V) and T-2-P1240(1Y) against CF-PAC-1 cells was shown to be HLA-A2-restricted, as indicated by the inhibition of lysis with anti-HLA-A2 antibody but not with the control antibody UPC-10 (Table 6).

TABLE 6

HLA-A2-specific inhibition of tumor cell lysis by T-cell lines.

|  | Lysis[#] |
|---|---|
| Treatment of T-4-P1177(10V) | |
| None | 23.4 (1.9) |
| Anti-HLA-A2 | 7.4 (1.7)* |
| UPC-10 (negative control) | 20.8 (3.1) |
| Treatment of T-4-P1240(1Y) | |
| None | 16.6 (1.2) |
| Anti-HLA-A2 | 5.6 (2.0)* |
| UPC-10 (negative control) | 13.6 (1.5) |

*$p < 0.01$ by t-test of lysis with or without peptide.
[#]Results are expressed as percent specific lysis at 25:1 E:T ratio (SD).

These results showed that MUC1-C-specific T cells generated using agonist epitopes lyse tumor cells that endogenously express native MUC-1 in an antigen-specific and HLA-A2-restricted manner.

Example 6

The following materials and methods were used for the experiments discussed in Examples 7-9.

Patients

Peripheral blood mononuclear cells (PBMCs) from ovarian cancer patients enrolled in a previously described clinical trial of a CEA- and MUC1-based viral vaccine (PANVAC-V/F) (Gulley et al., *Clin. Cancer Res.*, 14: 3060-3069 (2008)) were used. PANVAC consists of recombinant vaccinia (V) and fowlpox (F) vectors expressing CEA, MUC1 and three costimulatory molecules (B7.1, intercellular adhesion molecule 1 (ICAM-1), and lymphocyte function-associated antigen 3 (LFA-3)). It was given with vaccinia as prime, and fowlpox as boost injections every other week for the first month, and monthly thereafter.

PBMCs from an HLA-A3+ healthy donor were used as a reference population where indicated. An institutional review board of the National Institutes of Health Clinical Center had approved the procedure, and informed consent was obtained in accordance with the Declaration of Helsinki.

Cell Cultures

The human ovarian carcinoma cell line SKOV3 (HLA-A3+ and MUC1+), and pancreatic carcinoma cell lines CFPAC1 (HLA-A3+ and MUC1+) and ASPC-1 (HLA-A3+ and MUC1−) were purchased from American Type Culture Collection (Manassas, Va.). All cell cultures were free of *mycoplasma* and maintained in complete medium (RPMI 1640 supplemented with 10% fetal calf serum, 100 U/ml penicillin, 100 μg/ml streptomycin and 2 mM L-glutamine) (Mediatech, Herndon, Va.). C1RA3 and K562-A3 cells: C1R (kind gift from Dr. WE Biddison (NINDS, NIH, Bethesda, Md.)) and K562 (ATCC) were transfected with an HLA-A3 vector to express HLA-A3 by the NCI-Fredrick Eukaryotic Expression Group (Frederick, Md.). They were maintained in complete RPMI medium supplemented with 0.2 mg/ml of G-418 (Mediatech).

Peptides

The MUC1-C amino acid sequence was scanned for matches to consensus motifs for HLA-A3 binding peptides using the computer algorithm developed by Parker et al. to rank potential MHC-binding peptides according to the predicted one-half-time dissociation of peptide/MHC complexes (Parker et al., *J. Immunol.*, 152: 163-175 (1994)). American Peptide Company (Sunnyvale, Calif.) synthesized seven 9-mer or 10-mer peptide analogues from MUC1-C with amino acid substitutions in order to increase the binding affinity. The purity of the peptides was >90%.

Culture of Dendritic Cells from PBMCs

Peripheral blood was collected from patients, and PBMCs were isolated by centrifugation on a density gradient (Lymphocyte Separation Medium, ICN Biochemicals, Aurora, Va.). Dendritic cells (DCs) were generated using a modification of the previously described procedure (Yokokawa et al., *Int. J. Cancer*, 121: 595-605 (2007)). DCs were grown in AIM-V medium containing 100 ng/ml GM-CSF and 20 ng/ml IL-4 (PeproTech, Rocky Hill, N.J.). After 5 days in culture the DCs were matured by addition of 1 μg/ml CD40L and 1 μg/ml enhancer (Enzo Life Sciences, Farmingdale, N.Y.) for 24 h. They were then either used immediately for the first in vitro stimulation of PBMCs (IVS1), or frozen in aliquots for future use.

Generation of T-Cell Lines

A modified version of the protocol described by Tsang et al., *J. Nat. Cancer Inst.*, 87: 982-990 (1995), was used to generate MUC1-C specific cytotoxic T-lymphocytes. Irradiated autologous DCs were pulsed with 12.5 μg/ml of peptide for 2 h, and then PBMCs were added at a 10:1 ratio. After 3 days human IL-2 (20 Cetus units/ml) was added. Cells were restimulated every 7 days. After the third in vitro stimulation (IVS), cells were restimulated using autologous Epstein-Barr virus transformed B-cells as antigen presenting cells, at a ratio of 3:1.

Flow Cytometry

Flow cytometric analysis (FACS) was performed as previously described (Yokokawa et al., supra). Briefly, the GAP-A3 antibody with a goat anti-human secondary FITC-conjugated antibody was used for HLA-A3, and the DF3 antibody was used for extracellular MUC-1. Four-color FACS analysis was performed on T-cell lines by staining for 40 minutes at 4° C. with CD8-PE, CD45RA-PECy7, CD62L-FITC and CXCR3-APC (BD Biosciences, San Jose, Calif.). $1 \times 10^5$ cells were acquired on an LSRII (BD), and data was analyzed using FlowJo 9.0.1 software (Tree Star Inc, Ashland, Oreg.). The appropriate isotype controls were used, and dead cells were excluded from the analysis.

Tetramer Staining

Phycoerythrin (PE) labeled HLA-A3-P432-3F10K and HLA-A3-P483-2L3F tetramers were prepared by the NIH Tetramer Core Facility (Atlanta, Ga.), and PE labeled MHC class I human negative tetramer (Kit No T01044) was obtained from Beckman Coulter Inc (Sykesville, Md.). The negative tetramer has no known specificity and does not bind to human CD8+ T-cells of any HLA allele. The tetramers were used at a 1:100 dilution, and cells were stained for 45 minutes at 4° C. $1 \times 10^5$ cells were acquired on an LSRII (BD), and data was analyzed using FlowJo 9.0.1 software (Tree Star Inc, Ashland, Oreg.).

Cytotoxicity Assay and Cold Target Inhibition Assay

To determine T-cell mediated killing a 16-hour [111]Indium release assay was used (Tsang et al., supra). $2 \times 10^6$ target cells were labeled with 60 μCi $^{111}$In oxide (GE Health care, Vienna, Va.) at 37° C. for 20 minutes, and used at 3000 cells/well in 96-well round-bottom culture plates. T-cells were added at different ratios. All assays were performed in RPMI medium substituted with 10% fetal bovine serum, glutamine, and antibiotics (Mediatech, Manassas, Va.). Spontaneous release was determined by incubating target cells with medium alone, and complete lysis by incubation with 2.5% Triton X-100. Lysis was calculated using the formula (all values in cpm):

$$\% \text{ lysis} = \frac{\text{Observed release}(cpm) - \text{spontaneous release}}{\text{Complete release}(cpm) - \text{spontaneous release}} \times 100$$

A cold target inhibition assay was performed by adding K562-A3 cells or peptide-pulsed K562-A3 cells at a ratio of 1:10 to the wells (Yokokawa et al., supra).

Detection of Cytokines $2.2 \times 10^6$ T-cells and $5.5 \times 10^6$ autologous B-cells pulsed with peptide P432-3F10K or P483-2L3F were incubated for 24 h in 5 ml medium per well. The supernatants were analyzed by Multi-array technology (Meso Scale Diagnostics, Gaitersburg, Md.) for detection of cytokines.

ELISPOT Assay

Measurement of CD8 immune responses in HLA-A3+ patients was conducted by enzyme-linked immunosorbent spot assay (ELISPOT) using a modification of the procedure described in Arlen et al., Cancer Immunol. Immunother., 49: 517-529 (2000). The assay was performed using K562-A3 cells as APC. ELISPOT measures the frequency of T cells releasing IFNγ in response to stimulation with a peptide. P432-3F10K, P483-2L3F, no peptide, or an HIV gag peptide (SEQ ID NO: 25; a negative control) were used. Pre- and Post-vaccination PBMCs from each patient were compared. A positive response was scored as a ≥2-fold increase in IFNγ-secreting cells. The spots were analyzed using an ImmunoSpot counter (Cellular Technology Ltd, Shaker Heights, Ohio).

Statistical Analysis

For statistical evaluation, the non-parametric Mann-Whitney test was used between two groups (GraphPad Software, La Jolla, Calif.). A P value <0.05 was considered significant.

Example 7

This example demonstrates the determination of CTL epitopes of MUC1-C subunit and analogs thereof.

The MUC1-C amino acid sequence was scanned for matches to consensus motifs for HLA-A3 binding peptides in order to identify possible CD8+ T-cell epitopes that could be used for immunotherapy. Since the predicted binding of the native epitopes was low, seven new peptides with higher predicted binding to the T-cell receptor were prepared (see Table 7).

These peptides were investigated for their ability to generate cytotoxic T-lymphocytes (CTL). CTL were generated by in vitro stimulations of PBMCs, which were then used in a cytotoxicity assay with peptide-pulsed C1RA3 cells as targets. The cell lines generated with two peptides, designated T-432-3F10K and T-483-2L3F (corresponding to P432-3F10K and P483-2L3F, respectively), demonstrated high cytotoxic activity, and these peptides were used in subsequent experiments.

To determine the frequency of MUC1-C specific CD8+ T-cells in the T-cell lines generated with peptides P432-3F10K and P483-2L3F, HLA-A3-P432-3F10K tetramer and HLA-A3-P483-2L3F tetramer analysis was used. After 6 IVS cycles, 20% and 16% of the T-cells bound to the P432-3F10K and P483-2L3F tetramer, respectively. 0.01% and 0.04% of the cells bound to a negative tetramer.

To test the ability of the MUC1-C peptides to induce cytokine production, P432-3F10K and P483-2L3F specific T-cell lines ($1.1 \times 10^6$ T cells/mL) from two patients from the PANVAC ovarian cancer clinical trial described in Example 6 were incubated for 24 hours with autologous B-cells pulsed with P432-3F10K or P483-2L3F for 24 hours. The cytokine levels in supernatant of stimulated and unstimulated cells were evaluated. As shown in Table 8, there was an increase in several Type I cytokines after stimulation.

TABLE 8

Cytokine production by MUC1-C specific T-cell lines generated from two ovarian cancer patients using peptides P432-3F10K and P483-2L3F.

| Patient | Peptide | IVS | IL-2* | IL-12p70* | IFNγ* | IL-6* | TNFα* |
|---|---|---|---|---|---|---|---|
| I | P432-3F10K | 7 | 40 | 5 | 350 | 16 | 180 |
|   | P483-2L3F | 7 | 7 | 5 | 180 | 12 | 46 |
| II | P432-3F10K | 8 | 3 | 7 | 50 | 80 | 130 |
|   | P483-2L3F | 8 | 15 | 9 | 2590 | 150 | 470 |

*Values expressed as pg/mL

TABLE 7

Binding of MUC1-C native and agonist peptides to the HLA-A3 molecule.

| Peptide* | Sequence | SEQ ID NO: | Amino Acid Position in MUC1 | Predicted Binding# |
|---|---|---|---|---|
| Native 432 | ALAIVYLIAL | 1 | 1172 | 5.4 |
| P432-3F10K | ALFIVYLIAK | 10 | 1172 | 900 |
| Native 483 | STDRSPYEK | 12 | 1223 | 3.0 |
| P483-2L3Y | SLYRSPYEK | 13 | 1223 | 300 |
| P483-2L3F | SLFRSPYEK | 14 | 1223 | 300 |
| Native 423 | LLVLVCVLVA | 18 | 1163 | 1.35 |
| P423-6I/10K | LLVLVIVLVK | 19 | 1163 | 270 |
| P423-10K | LLVLVCVLVK | 20 | 1163 | 180 |
| Native 440 | GQLDIFPAR | 21 | 1192 | 4.00 |
| P440-3F/7I/9K | GLLDIFPAK | 22 | 1192 | 200 |
| Native 452 | GQLDIFPAR | 23 | 1204 | 2.43 |
| P452-2L/9K | GLLDIFPAK | 24 | 1204 | 405 |

Example 8

This example demonstrates the ability of the inventive peptides to inhibit cancer cells.

After 4 or 6 IVS, the peptide-specific T-cell lines from two cancer patients were examined in a cytotoxicity assay. The human ovarian carcinoma cell line SKOV3, and the pancreatic carcinoma cell line ASPC-1 were stained with antibodies against HLA-A3 and MUC1 for FACS analysis. SKOV expressed HLA-A3 (99%) and MUC1 (94%), whereas ASPC-1 was MUC1 positive (71%), but did not express HLA-A3.

The cancer cell lines were incubated with radioactive Indium ($^{111}$In), and used in a cytotoxicity assay with the specific T-432-3F10K and T-483-2L3F T-cell lines. The T-cells specifically killed tumor cells expressing both MUC1 and HLA-A3, but not MUC1-expressing cells with no HLA-A3.

In addition, a cold target inhibition assay was performed with the pancreatic carcinoma cell line CF-PAC-1 (HLA-A3$^+$ and MUC1$^+$) as a target, and peptide-pulsed K562-A3 cells as cold targets. These cells efficiently present peptides, and when added at a 1:10 ratio block the lysis of the tumor cells, whereas K562-A3 cells that had not been exposed to peptide did not affect the tumor lysis when added at the same concentration (see FIGS. 2A-B). The T-cell:target cell ratio was 25:1.

Example 9

This example demonstrates the immunogenicity of the inventive peptides in cancer patients.

PBMCs from three patients from the clinical vaccine trial were stimulated for 2 IVS cycles with the autologous dendritic cells exposed to peptide P432-3F10K or P483-2L3F, and one week after the last stimulation the cells were subjected to FACS analysis after staining with CD8-FITC (20 μL) and either P432-3F10K/P483-2L3F-tetramer-PE (1 μL) or negative tetramer-PC (1 μL) for 45 minutes.

As shown in Tables 9 and 10, 20-60% of the cells bound to the tetramers after 2 stimulations. Results in Tables 9 and 10 are expressed as the frequency of tetramer positive cells from all CD8$^+$ T-cells.

TABLE 9

Identification of P432-3F10K-specific CD8+ T cells with tetramers in PBMCs from cancer patients.

| Sample | P432-3F10K-tetramer (%) | Negative tetramer (%) |
|---|---|---|
| Cancer patient pre-vaccination | | |
| III | 44.5 | 0.30 |
| IV | 22.0 | 0.18 |
| V | 31.5 | 0.08 |
| Cancer patient post-vaccination | | |
| III | 59.9 | 3.4 |
| IV | 23.8 | 0.25 |
| V | 22.0 | 0.30 |

TABLE 10

Identification of P483-2L3F-specific CD8+ T cells with tetramers in PBMCs from cancer patients.

| Sample | P483-2L3F-tetramer (%) | Negative tetramer (%) |
|---|---|---|
| Cancer patient pre-vaccination | | |
| III | 64.7 | 0.00 |
| IV | 45.5 | 0.50 |
| V | 53.5 | 0.15 |
| Cancer patient post-vaccination | | |
| III | 80.9 | 0.46 |
| IV | 65.7 | 0.47 |
| V | 43.8 | 0.24 |

To evaluate the presence of CD8$^+$ T-cells reactive to the P432-3F10K and P483-2L3F peptides in PBMCs from carcinoma patients enrolled in the clinical vaccine trial, an IFNγ ELISPOT assay was performed. The P432-3F10K and P483-2L3F peptides were used in an ELISPOT assay at a concentration of 25 μg/mL to determine the precursor frequency of specific T-cells. Peptide-pulsed K562-A3 cells were used as APC at an effector:APC ratio of 1:2. HIV peptide and no peptide were used as controls.

As shown in Table 11, 5 of 11 patients exhibited specific IFNγ production upon stimulation with peptide P432-3F1 OK in PBMCs from pre and three months postvaccination. No patient had a specific reaction to the P483-2L3F peptide, and patient I could not be evaluated because of too few PBMCs.

TABLE 11

Precursor frequency of T-cells specific for P432-3F10K and P483-2L3F in peripheral blood from patients with MUC1 and CEA expressing tumors before and after vaccination with PANVAC.

| Patient | Time Point | P432-3F10K | P483-2L3F |
|---|---|---|---|
| Patient II | Pre | 1/6316 | <1/200000 |
| | Post | 1/2372 | <1/200000 |
| Patient III | Pre | 1/6522 | <1/200000 |
| | Post | 1/5455 | <1/200000 |
| Patient IV | Pre | 1/2000 | <1/200000 |
| | Post | 1/1322 | <1/200000 |
| Patient V | Pre | <1/200000 | <1/200000 |
| | Post | <1/200000 | <1/200000 |
| Patient VI | Pre | 1/4511 | <1/200000 |
| | Post | 1/21429 | <1/200000 |
| Patient VII | Pre | <1/200000 | <1/200000 |
| | Post | <1/200000 | <1/200000 |
| Patient VIII | Pre | <1/200000 | <1/200000 |
| | Post | <1/200000 | <1/200000 |
| Patient IX | Pre | <1/200000 | <1/200000 |
| | Post | <1/200000 | <1/200000 |
| Patient X | Pre | <1/200000 | <1/200000 |
| | Post | <1/200000 | <1/200000 |
| Patient XI | Pre | 1/4196 | <1/200000 |
| | Post | 1/7229 | <1/200000 |

Example 10

The following materials and methods were used for the experiments discussed in Examples 11 and 12.

Peptide Binding to HLA-A2

Binding of pVNTR1, pVNTR2, pVNTR4, and their analogs (pVNTR3 and pVNTR5) to HLA-A2 molecules was evaluated by the upregulation of HLA-A2 expression on T2A2 cells, as demonstrated by flow cytometry (Nijman et al., *Eur. J. Immunol.*, 23: 1215-1219 (1993)).

Generation of T-Cell Lines

MUC1-C-specific CTLs were generated by a modification of the protocol described by Tsang et al., *J. Nat. Cancer Inst.*, 87: 982-990 (1995). pVNTR3-, pVNTR5-specific T-cell lines were generated from a prostate patient vaccinated with a PSA-based vaccine. CD40L or yeast-matured autologous DCs, generated as previously described, were used as antigen-presenting cells (APCs). PBMCs obtained on day 94 post-vaccination were added to the APCs and pulsed with 12.5 μg/mL of the corresponding peptide at an effector:APC ratio of 10:1. Autologous DCs were used as APCs for 3 in vitro stimulation (IVS) cycles. Irradiated (23,000 rads) autologous EBV-transformed B cells were used as APCs after the third IVS cycle. For restimulation with EBV-transformed B cells, peptides at a concentration of 12.5 μg/mL were used to pulse the autologous EBV-transformed B cells at an effector:APC ratio of 1:3. Cultures were incubated for 3 days at 37° C. in a humidified atmosphere containing 5% $CO_2$. The cultures were then supplemented with recombinant human IL-2 at a concentration of 20 U/mL for 7 days; the IL-2-containing medium was replenished every 3 days. The 3-day incubation with peptide and 7-day IL-2 supplement constituted one IVS cycle.

Cytotoxic Assay

Target cells were labeled with 50 μCi of $^{111}$In-labeled oxyquinoline (Medi-Physics Inc., Arlington, Ill.) for 15 min at room temperature. Target cells ($3 \times 10^3$) in 100 μL of RPMI-1640 complete medium were added to each of 96 wells in flat-bottomed assay plates. Effector cells were suspended in 100 μL, of RPMI-1640 complete medium supplemented with 10% pooled human AB serum and added to the target cells. The plates were then incubated at 37° C. in 5% $CO_2$ for 4 or 16 h. Supernatant was harvested for gamma counting with the use of harvester frames (Skatron, Inc., Sterling, Va.). Determinations were carried out in triplicate, and standard deviations were calculated. Specific lysis was calculated according to the following formula (all values in cpm):

$$\% \text{ lysis} = \frac{\text{Observed release} - \text{spontaneous release}}{\text{Total release} - \text{spontaneous release}} \times 100$$

Spontaneous release was determined from wells to which 100 μL, of RPMI-1640 complete medium were added. Total releasable radioactivity was obtained after treatment of targets with 2.5% Triton X-100.

Cell Cultures

The MCF-7 human breast adenocarcinoma cell line ($HLA-A2^+/MUC1^+$), the CF-PAC-1 human pancreatic adenocarcinoma cell line ($HLA-A2^+/MUC1^+$), the SK-Mel-24 melanoma cell line ($HLA-A2^+/MUC1^-$), and the ASPC-1 human pancreatic adenocarcinoma cell line ($HLA-A2^-/MUC1^+$) were purchased from American Type Culture Collection (Manassas, Va.) and maintained in DMEM complete medium (Mediatech, Inc., Manassas, Va.) supplemented with 10% fetal bovine serum, 2 mM glutamine, 100 units/mL penicillin, 100 μg/mL streptomycin, 0.5 μg/mL amphotericin B (Mediatech, Inc.), and 0.01 μg/mL human recombinant insulin (Invitrogen Life Technologies, Inc., Carlsbad, Calif.). All cultures were *Mycoplasma*-free.

Example 11

This example demonstrates the determination of CTL epitopes of MUC1 VNTR region and analogs thereof.

The MUC1 VNTR amino acid sequence was scanned for matches to consensus motifs for HLA-A2 binding peptides in order to identify possible $CD8^+$ T-cell epitopes that could be used for immunotherapy. Three 9-mer peptides (designated VNTR-1, VNTR-2, and VNTR-4) were identified and synthesized (see Table 12).

Two analogs of native epitopes VNTR-2 and VNTR-4 (VNTR-3 and VNTR-5, respectively) were generated by amino acid substitutions at the amino acid residues at positions 1, 2, and 9 (see Table 12). Each of the analogs had a predicted higher affinity for HLA-A2 molecules than the corresponding native epitopes.

A peptide with a high affinity for HLA-A2 molecules (NGEP P703) (Cereda et al., *Cancer Immunol. Immunother.*, 59: 63-71 (2010)) and a specific HLA-A3 peptide (CAP-7) were used in the assays as positive and negative controls, respectively.

TABLE 12

Binding of MUC1 VNTR peptides to HLA-A2 molecules.

| Peptide* | Amino Acid Sequence | SEQ ID NO: | Predicted Binding | T2A2 Binding[#] |
|---|---|---|---|---|
| VNTR-1 | STAPPAHNV | 27 | 0.966 | 169.0 |
| VNTR-2 | STAPPAHGV | 28 | 0.966 | 165.7 |
| VNTR-3 (agonist) | YLAPPAHGV | 29 | 319.9 | 485.5 |
| VNTR-4 | APDTRPAPG | 31 | 0 | 209.7 |
| VNTR-5 (agonist) | YLDTRPAPV | 32 | 127.9 | 647.4 |
| NGEP (P703) (positive control) | GLFDEYLEMV | 16 | NA | 485.3 |
| CAP-7 (negative control) | HLFGYSWYK | 17 | NA | 83.8 |

*Peptides were used at a concentration of 25 μg/mL.
[#]Results expressed as mean fluorescence intensity (MFI).

VNTR-1, VNTR-2, and VNTR-4 showed a greater affinity for HLA-A2 molecules compared to the negative control. Analog peptides VNTR-3 and VNTR-5 showed a greater affinity for HLA-A2 molecules compared to the corresponding native peptides VNTR-2 and VNTR-4, respectively.

The stability of the peptide/HLA-A2 complexes of the analogs and native peptides was analyzed by determining the percentage of the remaining complexes on HLA-A2 molecules at different time points (0, 2, 4, 6, 8, and 10 h). The analog peptides VNTR-3 and VNTR-5 demonstrated a greater avidity for class I molecules than the native peptides VNTR-2 and VNTR-4, respectively, at each time point (see FIG. 3).

Example 12

This example demonstrates the immunogenicity of the MUC1 VNTR enhancer analog peptides in cancer patients.

VNTR-3 and VNTR-5 peptides were investigated for their ability to generate CTLs by in vitro stimulations of PBMCs. The resulting T-cell lines (T-VNTR-3 and T-VNTR-5, respectively) were then tested for cytotoxic activity against a MUC1$^+$/HLA-A2$^+$ breast carcinoma cell line (MCF-7) and a MUC1$^+$/HLA-A2$^+$/A3$^+$ pancreatic cancer cell line (CF-PAC-1). A MUC1$^-$/HLA-A2$^+$ melanoma cell line (SK-MEL) and a MUC1$^+$/HLA-A2$^-$ pancreatic cancer cell line (ASPC-1) were used as negative controls.

An $^{111}$In release assay was performed using MUC1 VNTR epitope-specific T-cell lines. As expected, no lysis was observed against ASPC-1 (HLA-A2$^-$) and SK-MEL (MUC1$^-$) cells (see Table 13).

TABLE 13

VNTR-specific T cells kill tumor cells expressing HLA-A2 and MUC-1.

| T cell line | E:T ratio | MCF-7 (HLA-A2$^+$ MUC1$^+$)[#] | CF-PAC-1 (HLA-A2$^+$/A3$^+$ MUC1$^+$)[#] | ASPC-1 (HLA-A2$^-$ MUC1$^+$)[#] | SK-MEL (HLA-A2$^+$ MUC1$^-$)[#] |
|---|---|---|---|---|---|
| T-VNTR-3 | 25:1 | 42.2 (7.3) | 16.9 (3.6) | 1.3 (1.9) | 5.0 (2.5) |
|  | 12.5:1 | 24.6 (3.5) | 10.9 (1.3) | −0.8 (0.6) | −1.5 (2.1) |
| T-VNTR-5 | 25:1 | 53.4 (8.4) | 48.9 (4.9) | −0.8 (0.4) | −0.6 (4.3) |
|  | 12.5:1 | 45.1 (3.0) | 31.2 (2.4) | −1.4 (0.6) | 1.5 (0.5) |

[#]Results are expressed as percent specific lysis (standard deviation).

T-VNTR-3 (VNTR-3 agonist peptide-specific T cell line) and T-VNTR-5 (VNTR-5 agonist peptide-specific T cell line) were separately cultured at a concentration of 1×10$^5$ cells/mL. The ratio of APC:T cells was 3:1. The agonist or native peptides were used at various concentrations (see Tables 14 and 15). The supernatents were collected after 24 hours, and the amount of IFN-γ was determined. The VNTR-3- and VNTR-5-specific T cell lines stimulated with agonist peptides produced higher levels of IFN-γ as compared to stimulation with native peptides (see Tables 14 and 15).

TABLE 14

VNTR-3-specific T cell line stimulated with agonist peptides produced higher levels of IFN-γ.

| | Concentration of Peptide (μg/mL) | | | | | |
|---|---|---|---|---|---|---|
| Peptide | 25[#] | 12.5[#] | 6.25[#] | 3.13[#] | 1.56[#] | 0[#] |
| VNTR-3 (agonist) | 771.5 | 766.1 | 685.3 | 457.6 | 304.9 | <15.6 |

TABLE 14-continued

VNTR-3-specific T cell line stimulated with agonist peptides produced higher levels of IFN-γ.

| | Concentration of Peptide (μg/mL) | | | | | |
|---|---|---|---|---|---|---|
| Peptide | 25[#] | 12.5[#] | 6.25[#] | 3.13[#] | 1.56[#] | 0[#] |
| VNTR-2 (native) | 261.0 | 203.0 | 127.0 | 75.8 | 29.0 | <15.6 |

[#]Results are expressed in pg/mL of IFN-γ.

TABLE 15

VNTR-5-specific T cell line stimulated with agonist peptides produced higher levels of IFN-γ.

| | Concentration of Peptide (μg/mL) | | | | | |
|---|---|---|---|---|---|---|
| Peptide | 25[#] | 12.5[#] | 6.25[#] | 3.13[#] | 1.56[#] | 0[#] |
| VNTR-5 (agonist) | 543.7 | 496.2 | 452.9 | 322.0 | 205.1 | <15.6 |
| VNTR-4 (native) | 117.9 | 109.3 | 63.1 | 53.2 | 19.8 | <15.6 |

[#]Results are expressed in pg/mL of IFN-γ.

To confirm the specificity and HLA-A2 restriction of CTL cytolysis, T-VNTR-3 and T-VNTR-5 cells were used in a cold target inhibition assay with the pancreatic carcinoma cell line CF-PAC-1 (HLA-A2$^+$/A3$^+$ and MUC1$^+$). CF-PAC-1 cells and autologous B cells that had or had not been pulsed with VNTR agonist peptides were used as targets.

As demonstrated by the data in Table 16, autologous B cells pulsed with the corresponding VNTR agonist peptide block the lysis of the tumor cells, whereas autologous B cells that had not been exposed to peptide did not affect the tumor lysis.

TABLE 16

Inhibition of lysis of CF-PAC-1 by MUC1-specific T-cell lines.

| Target Cells | MUC1 agonist peptide (pVNTR-3)-specific T cell (T-VNTR-3)[#] | MUC1 agonist peptide (pVNTR-5)-specific T cell (T-VNTR-5)[#] |
|---|---|---|
| CF-PAC-1 + B | 38.3 (3.5) | 25.8 (1.9) |
| CF-PAC-1 + B + pVNTR-3 | 16.0 (10.0) | — |
| CF-PAC-1 + B + pVNTR-5 | — | 12.0 (3.7) |

[#]Results are expressed as percent specific lysis (SD).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of enhancing an immune response against a MUC1-expressing cancer in a subject comprising administering to the subject a therapeutically effective amount of a composition comprising
   (i) a poxvirus vector comprising a nucleic acid encoding a peptide comprising at least one amino acid sequence selected from the group consisting of SEQ ID NO: 2, SEQ ID NO: 5, SEQ ID NO: 8, SEQ ID NO: 10, SEQ ID NO: 13, SEQ ID NO: 14, SEQ ID NO: 29, and SEQ ID NO: 32, or
   (ii) a liposome comprising a peptide comprising at least one amino acid sequence selected from the group consisting of SEQ ID NO: 2, SEQ ID NO: 5, SEQ ID NO: 8, SEQ ID NO: 10, SEQ ID NO: 13, SEQ ID NO: 14, SEQ ID NO: 29, and SEQ ID NO: 32,
   wherein the immune response in the subject is enhanced.

2. The method of claim 1, wherein the poxvirus vector is selected from the group consisting of orthopoxvirus, avipox, capripox, and suipox virus.

3. The method of claim 1, wherein the peptide comprises at least two of the amino acid sequences selected from the group consisting of SEQ ID NO: 2, SEQ ID NO: 5, SEQ ID NO: 8, SEQ ID NO: 10, SEQ ID NO: 13, SEQ ID NO: 14, SEQ ID NO: 29, and SEQ ID NO: 32.

4. The method of claim 1, wherein the peptide comprises at least three of the amino acid sequences selected from the group consisting of SEQ ID NO: 2, SEQ ID NO: 5, SEQ ID NO: 8, SEQ ID NO: 10, SEQ ID NO: 13, SEQ ID NO: 14, SEQ ID NO: 29, and SEQ ID NO: 32.

5. The method of claim 1, wherein the peptide comprises SEQ ID NO: 2, SEQ ID NO: 5, SEQ ID NO: 8, SEQ ID NO: 14, SEQ ID NO: 29, and SEQ ID NO: 32.

6. The method of claim 1, wherein the poxvirus vector further comprises a nucleic acid encoding at least one immunostimulatory/regulatory molecule.

7. The method of claim 6, wherein the at least one immunostimulatory/regulatory molecule is selected from the group consisting of interleukin (IL)-2, IL-4, IL-6, IL-12, interferon (IFN)-γ, tumor necrosis factor (TNF)-α, B7.1, B7.2, ICAM-1, LFA-3, CD70, RANTES, G-CSF, OX-40L, 41 BBL, anti-CTLA-4, and combinations thereof.

8. A method of enhancing an immune response against a MUC1-expressing cancer in a subject comprising:
   (a) administering to the subject a therapeutically effective amount of a first recombinant poxvirus vector comprising a nucleic acid encoding a peptide; and
   (b) administering to the subject a therapeutically effective amount of a second recombinant poxvirus vector comprising a nucleic acid encoding a peptide;
   wherein the peptides of (a) and (b) are the same and comprise at least one of the amino acid sequences selected from the group consisting of SEQ ID NO: 2, SEQ ID NO: 5, SEQ ID NO: 8, SEQ ID NO: 10, SEQ ID NO: 13, SEQ ID NO: 14, SEQ ID NO: 29, and SEQ ID NO: 32, and
   wherein the immune response in the subject is enhanced.

9. The method of claim 8, wherein the peptide comprises at least two amino acid sequences selected from the group consisting of SEQ ID NO: 2, SEQ ID NO: 5, SEQ ID NO: 8, SEQ ID NO: 10, SEQ ID NO: 13, SEQ ID NO: 14, SEQ ID NO: 29, and SEQ ID NO: 32.

10. The method of claim 8, wherein the peptide comprises the amino acid sequences of SEQ ID NO: 2, SEQ ID NO: 5, SEQ ID NO: 8, SEQ ID NO: 10, SEQ ID NO: 13, SEQ ID NO: 14, SEQ ID NO: 29, and SEQ ID NO: 32.

11. The method of claim 8, wherein the first and second recombinant poxvirus vectors each further comprise a nucleic acid encoding at least one immunostimulatory/regulatory molecule.

12. The method of claim 11, wherein the at least one immunostimulatory/regulatory molecule is selected from the group consisting of interleukin (IL)-2, IL-4, IL-6, IL-12, interferon (IFN)-γ, tumor necrosis factor (TNF)-α, B7.1, B7.2, ICAM-1, LFA-3, CD70, RANTES, G-CSF, OX-40L, 41 BBL, anti-CTLA-4, and combinations thereof.

13. The method of claim 8, wherein the first and second recombinant poxvirus vectors are selected from the group consisting of orthopox, avipox, capripox, and suipox virus.

14. The method of claim 13, wherein the first recombinant poxvirus vector is an orthopox virus and the second poxvirus recombinant vector is an avipox virus.

15. The method of claim 10, wherein the first and second recombinant poxvirus vectors each further comprise a nucleic acid encoding at least one immunostimulatory/regulatory molecule.

16. The method of claim 15, wherein the at least one immunostimulatory/regulatory molecule is selected from the group consisting of B7.1, B7.2, ICAM-1, LFA-3.

17. A method of enhancing an immune response against a MUC1-expressing cancer in a subject comprising administering to the subject a therapeutically effective amount of a composition comprising a poxvirus vector comprising a nucleic acid encoding a peptide comprising at least one amino acid sequence selected from the group consisting of SEQ ID NO: 2, SEQ ID NO: 5, SEQ ID NO: 8, SEQ ID NO: 10, SEQ ID NO: 13, SEQ ID NO: 14, SEQ ID NO: 29, and SEQ ID NO: 32, wherein the immune response in the subject is enhanced.

18. The method of claim 17, wherein the poxvirus vector is selected from the group consisting of orthopoxvirus, avipox, capripox, and suipox virus.

19. The method of claim 18, wherein the poxvirus vector is selected from the group consisting of an orthopoxvirus and an avipox.

20. The method of claim 19, wherein the poxvirus vector is an orthopoxvirus selected from the group consisting of vaccinia virus and a modified vaccinia Ankara (MVA) virus.

21. The method of claim 20, wherein the poxvirus vector further comprises a nucleic acid encoding at least one immunostimulatory/regulatory molecule.

22. The method of claim 21, wherein the at least one immunostimulatory/regulatory molecule is selected from the group consisting of B7.1, B7.2, ICAM-1, LFA-3.

23. The method of claim 1, wherein the composition comprises (ii) a liposome comprising a peptide comprising at least one amino acid sequence selected from the group consisting of SEQ ID NO: 2, SEQ ID NO: 5, SEQ ID NO: 8, SEQ ID NO: 10, SEQ ID NO: 13, SEQ ID NO: 14, SEQ ID NO: 29, and SEQ ID NO: 32.

24. The method of claim 23, wherein the composition comprises a liposome comprising a peptide comprising SEQ ID NO: 29.

25. The method of claim 23, wherein the composition comprises a liposome comprising a peptide comprising SEQ ID NO: 32.

* * * * *